United States Patent [19]
Masuya et al.

[11] Patent Number: 5,420,275
[45] Date of Patent: May 30, 1995

[54] PYRIDOPYRIDAZINE COMPOUNDS AND THEIR USE

[75] Inventors: Hirotomo Masuya, Kawabe; Yoshio Aramaki, Itami, both of Japan

[73] Assignee: Takeda Chemical Industries, Ltd., Osaka, Japan

[21] Appl. No.: 144,505

[22] Filed: Nov. 2, 1993

Related U.S. Application Data

[63] Continuation of Ser. No. 799,083, Nov. 27, 1991, abandoned.

[30] Foreign Application Priority Data

Nov. 27, 1990 [JP] Japan ................. 2-327777

[51] Int. Cl.⁶ ............... C07D 513/14; C07D 487/04; C07D 487/14; G01N 33/573
[52] U.S. Cl. .................. 544/236; 544/233; 544/234; 544/115; 544/117; 546/299; 546/310; 548/224; 548/228; 548/473; 435/7.1; 435/28; 436/92; 436/98; 436/528; 436/531; 530/391.3
[58] Field of Search ............. 544/233, 234, 236, 115, 544/117

[56] References Cited

U.S. PATENT DOCUMENTS

| | | | |
|---|---|---|---|
| 3,948,908 | 4/1976 | Yurugi et al. | 544/236 |
| 4,005,201 | 1/1977 | Yurugi et al. | 544/236 |
| 4,010,265 | 3/1977 | Yurugi et al. | 544/236 |
| 4,017,490 | 4/1977 | Yurugi et al. | 424/248.57 |

FOREIGN PATENT DOCUMENTS

| | | |
|---|---|---|
| 0175577 | 3/1986 | European Pat. Off. |
| 0313919 | 5/1989 | European Pat. Off. |
| 0331077 | 9/1989 | European Pat. Off. |
| 45-18458 | 6/1970 | Japan |
| WO9005915 | 5/1990 | WIPO |

OTHER PUBLICATIONS

Kondrat'Eva et al, Chemical Abstracts, vol. 54, No. 12131e (1960).
Miki et al, Chemical Abstracts, vol. 73, No. 77268h (1970). (Abstract for JP 70-18458).
YakugakuZasshi, No. 6, Matsuo et al., "Synthesis of Pyrido [3,4-d]pyridazine and a-Styrylpyridazine Derivatives from Dimethyl5-Hydroxy-6-methycinchomeronat" pp. 703–707. (1972).
Chem. Pharm. Bulletin, No. 11, vol. 24, No. 76, pp. 2699–2710, Omura et al., "Studieson the Syntheses of N–Heterocyclic Compounds.XXVIII. Syntheses of Pyrido[3,4–d]pyridazine Derivatives". (1976).

Primary Examiner—Emily Bernhardt
Attorney, Agent, or Firm—Foley & Lardner

[57] ABSTRACT

An assay method which comprises utilizing chemiluminescence of a pyridopyridazine compound of the formula

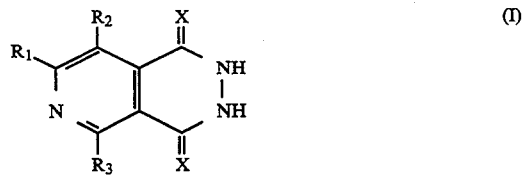

(I)

wherein $R_1$ is a hydrocarbon group or a heterocyclic group each of which may be substituted and $R_2$ is hydroxy group, thiol group, amino group or a monosubstituted amino group, and when $R_2$ is a monosubstituted amino group, $R_2$ may be taken together with $R_1$ to form the ring; $R_3$ is hydrogen atom, a hydroxy group which may be substituted, an amino group which may be substituted, a thiol group which may be substituted, a halogen atom, a heterocyclic group, nitro group, cyano group, carboxyl group which may be esterified or amidated, azido group, sulfo group or an organic sulfonyl group, provided that when $R_1$ is an aliphalic group, $R_3$ is not hydrogen atom; and X is oxygen atom or sulfur atom/or a salt thereof; and a novel compound of the formula (I) wherein the symbols are as defined above with proviso that $R_3$ is hydrogen atom, $R_1$ is a substituted aryl group or a heterocyclic group which may be substituted, or a salt thereof and the production methods thereof.

5 Claims, 4 Drawing Sheets

PYRIDOPYRIDAZINE COMPOUNDS AND THEIR USE

This application is a continuation of U.S. application Ser. No. 07/799,083, filed Nov. 27, 1991, now abandoned.

This invention relates to pyridopyridazine compounds which can be useful as chemiluminescent substances and to their use, more specifically, to high-sensitive assay methods using said pyridopyridazine compounds and diagnostic methods for tumors by the assay methods.

Analytical methods based on chemiluminescent reactions have the possibility to become an extremely high-sensitive method for detecting a chemical substance and have been intensively studied. Attention has been focussed on this analytical method especially in the field of immunological analysis, in which various kinds of techniques have been tried.

In the immunological analysis, a method using radioactive isotope assay (RIA) as a label has been developed at first, which however shows the disadvantages due to the use of radioactive isotopes, namely, a short half-life period, bio-hazard problems and, occasionally, insufficient sensitivity. Furthermore, a detecting method by colorimetric analysis or fluorescence analysis such as enzyme-immunological analysis using an enzyme as a label has been developed for overcoming the disadvantages accompanying RIA. However, development of new techniques was sought to achieve improvements in sensitivity. Among the new techniques, a method utilizing chemiluminescence is expected to be the most sensitive method and accordingly has been intensively studied.

Immunochemical analysis methods utilizing chemiluminescent reactions are generally classified into the following 4 methods [Akio Tsuji et al., Peptide, Nucleic Acid and Enzyme, Extra Issue, 31, 252–263 (1988)].

(1) A method labelling a chemically luminous substance such as luminol, isoluminol, acridinium derivative, etc., as a label compound on antibody or antigen.

(2) A method utilizing chemical luminous reaction for measuring enzyme activity which is labelled on antibody or antigen in the enzyme immunoassay (EIA) system.

(3) A homogeneous immunological analysis utilizing phenomenon of decrease of coenzyme activity by antigen-antibody reaction in which coenzyme, namely, NAD or ATP is labelled.

(4) Enzyme immunoassay method utilizing biological luminous reaction.

Among these methods, the method (1) involves some problems. That is, the sensitivity can not be improved as expected due to decline of luminous quantum yield caused by chemical combination of luminous substance, and measuring in a very short time of chemiluminescence is extremely difficult. The method (2) is a system in which the chemiluminescent substance exists in a free form from antigen or antibody in a solution and the label enzyme acts as the catalyst for luminous reaction, but its sensitivity is not entirely satisfactory.

Improvement of sensitivity by the above method (3) can not be expected, and the method (4) can not be generalized due to use of specific enzyme in many cases.

Though a number of studies of assays using chemiluminescent reaction have been carried out due to expectable high sensitivity as mentioned above, there have not been so far any practical assay system that afforded entirely satisfactory sensitivity.

A variety of studies have been conducted to solve the foregoing problem, and, one of them reported that it was essential to synthesize compounds which possess excellent chemiluminescent yields [Kazuhiro Imai, "Bioluminescence and Chemiluminescence" 1989, 75, Hirokawa Shoten.] While as such compounds, for example, lophine, luminol, lucigenin and their derivatives have been known, a number of researchers have been carrying out studies for identification and synthesis of chemiluminescent compounds having higher luminous quantum yield.

Among them, particularly active studies have been made of luminol and its derivatives. Chemiluminescence of luminol was found by Albrecht [Zeitschrift für Physikalische Chemie, 136, 321 (1928)], and of the luminescent compounds, luminol has been most widely used.

This invention is to provide assay methods using pyridopyridazine compounds of the formula

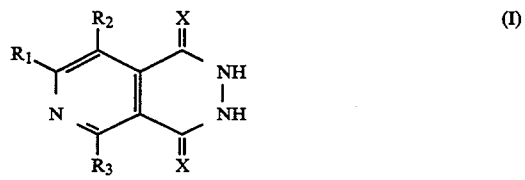

wherein $R_1$ is a hydrocarbon group or a heterocyclic group each of which may be substituted and $R_2$ is hydroxy group, thiol group, amino group or a monosubstituted amino group, and when $R_2$ is a monosubstituted amino group, $R_2$ may be taken together with $R_1$ to form the ring; $R_3$ is hydrogen atom, a hydroxy group which may be substituted, an amino group which may be substituted, a thiol group which may be substituted, a halogen atom, a heterocyclic group, nitro group, cyano group, carboxyl group which may be esterified or amidated, azido group, sulfo group or an organic sulfonyl group, provided that when $R_1$ is an aliphatic group, $R_3$ is not hydrogen atom; and X is oxygen atom or sulfur atom, or salts thereof.

Among the compounds of the formula (I) or salts thereof, novel are the compounds of the formula (I) wherein $R_3$ is other than hydrogen atom, or salts thereof and the compounds of the formula (I) wherein when $R_3$ is hydrogen atom, $R_1$ is a substituted aryl group or a heterocyclic group which may be substituted, or salts thereof. This invention is also to provide said novel compounds (hereinafter the novel compounds are sometimes referred to the compounds of the general formula (I')) and methods for production thereof.

Referring to the pyridopyridazine compounds of the above general formula (I), concrete examples of the hydrocarbon group represented by $R_1$ include straight chain or branched chain lower alkyl groups having 1 to 6 carbons such as methyl, ethyl, n-propyl, isopropyl, n-butyl, isobutyl, sec-butyl, tert-butyl, n-pentyl, isopentyl and hexyl; alkenyl groups having 2 to 3 carbon atoms such as vinyl and allyl; alkynyl groups having 2 to 3 carbon atoms such as ethynyl and propargyl; aralkyl groups having 7 to 12 carbon atoms such as benzyl and phenethyl; aryl groups having 6 to 10 carbon atoms such as phenyl and naphthyl. As examples of "the heterocyclic groups" represented by $R_1$, there may be mentioned 5- or 6-membered heterocyclic groups which contain at least one hetero atom of nitrogen, sulfur and oxygen, preferably one to four hetero atom(s). The heterocyclic groups may be saturated or unsaturated. Specific examples of the heterocyclic group include 2-pyridyl, 4-pyridyl, 2-thienyl, 2-furyl, imidazolyl, triazolyl, tetrazolyl, morpholino, piperazyl, 4-thiazolyl and 2-amino-4-thiazolyl.

As the substituents which $R_1$ may have, mention is made of the groups of the formula $$R_4 \text{ or } R_4\text{-(CH}_2\text{)}_n\text{-A-} \qquad \text{(IV)}$$

wherein $R_4$ is $-CN$, $-hal$, $-OPO_3M_2$, $-OSO_3M$, $-CO_2R_5$, $-SR_6$, $-OR_6$ or $-NHR_6$; A is sulfur, oxygen or nitrogen atom; n is an integer of 1 to 4; M is an alkali metal or hydrogen atom; hal is a halogen atom such as fluorine, chlorine, bromine or iodine; $R_5$ is hydrogen atom, a lower alkyl group such as methyl, ethyl or propyl, or a group forming an active imido ester capable of forming conjugate such as maleimido, succinimido or 5-norbornen-2, 3-carboxyimido group; and $R_6$ is hydrogen atom or a group forming an active imido ester e.g. succinic acid half ester capable of forming conjugate representable by the formula $$-COCH_2CH_2COOR_7 \qquad \text{(V)}$$

wherein $R_7$ represents maleimido, succinimido or 5-norbornen-2, 3-carboxyimido group.

As concrete examples of the substituent in the monosubstituted amino group represented by $R_2$ in the general formula (I), there can be mentioned straight chain or branched chain lower alkyl groups having 1 to 6 carbon atoms, alkenyl groups having 2 to 3 carbon atoms, alkynyl groups having 2 to 3 carbon atoms, aralkyl group having 7 to 12 carbon atoms and aryl groups having 6 to 10 carbon atoms as mentioned above in connection with $R_1$. As concrete examples of the compounds (I) wherein $R_2$ is a monosubstituted amino group which is taken together with the substituent $R_1$, to form a ring, there can be mentioned cyclic amines of the general formula

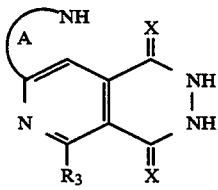

wherein $R_3$ and X are of the same meaning as defined above and ring A is a nitrogen-containing 5- to 7-membered ring which may have 1 to 2 unsaturated bonds such as imidazole, thiazole, pyrrole and pyridazine.or a nitrogen containing 5- to 7- membered ring which is fused with a benzene ring or a heterocyclic ring such as indole, benzofuran, quinoline and ring A may be substituted by lower alkyl groups having 1 to 6 carbon atoms such as methyl, ethyl and propyl.

As "the hydroxy group which may be substituted" represented by $R_3$, there may be mentioned, for example, hydroxy group, alkoxy groups, aryloxy groups and aralkyloxy groups. As examples of the alkyl group in the alkoxy group represented by the substituent $R_3$ in the formula (I), mention is made of such straight chain or branched chain lower alkyl groups having 1 to 6 carbon atoms as mentioned before for $R_1$. Examples of the aryl group in the aryloxy group represented by $R_3$ include aryl groups having 6 to 10 carbon atoms such as phenyl and examples of the aralkyl group in the aralkyloxy group include aralkyl groups having 7 to 12 carbon atoms such as benzyl.

As "the amino group which may be substituted" represented by $R_3$, there may be mentioned, for example, amino group, monosubstituted amino groups and disubstituted amino groups. Examples of the substituent in the monosubstituted amino group include such straight chain or branched chain lower alkyl groups having 1 to 6 carbon atoms as mentioned before for $R_1$; cycloalkyl groups having 3 to 6 carbon atoms such as cyclopropyl, cyclopentyl and cyclohexyl; alkenyl groups having 2 to 3 carbon atoms such as vinyl and allyl; alkynyl groups having 2 to 3 carbon atoms such as ethynyl and propargyl; aralkyl groups having 7 to 12 carbon atoms such as benzyl and phenethyl; and aryl groups having 6 to 10 carbon atoms such as phenyl and naphthyl. As the substituents in the disubstituted amino group, mention is made of the same or different substituents among the substituents such as mentioned above for the substituent in the monosubstituted amino group.

As "the thiol group which may be substituted" represented by $R_3$, there may be mentioned, for example, thiol group, alkylthio groups, arylthio groups and aralkylthio groups. As examples of the alkyl group in the alkylthio group, the aryl group in the arylthio group, and the aralkyl group in the aralkylthio group, there may be mentioned such groups as mentioned above respectively in connection with "the hydroxy group which may be substituted" represented by $R_3$.

Examples of the halogen atom represented by $R_3$ include iodine, bromine, chlorine and fluorine.

As examples of "the heterocyclic group" represented by $R_3$, there may be mentioned such heterocyclic groups as mentioned before for $R_1$.

As "the carboxyl group which may be esterified or amidated" represented by $R_3$, there may be mentioned, for example, carboxyl group, carbamoyl groups and alkoxycarbonyl groups. As the alkyl group in "the alkoxycarbonyl group" as "the esterified carboxyl group" represented by $R_3$, there may be mentioned such alkyl groups as mentioned above for $R_1$.

Examples of "the organic sulfonyl group" represented by $R_3$ include alkylsulfonyl groups and arylsulfonyl groups. As "the alkyl group" in the alkylsulfonyl and "the aryl group" in the arylsulfonyl group, there may be mentioned, for example, such alkyl groups and aryl groups as mentioned above for $R_1$ respectively. The aryl group, particularly the phenyl group may be substituted by a lower alkyl group such as methyl or ethyl.

The carbonyl or thiocarbonyl group of the pyridopyridazine ring as represented in the general formula (I) readily enolizes, forming a salt with a univalent or bivalent cation.

As examples of univalent cations, there may be mentioned ammonium ions and alkali metal ions. Specific examples of the ammonium ions, there may be mentioned, for example, those of ammonia, $C_{1-4}$ mono alkylamine such as methyl amine, ethyl amine and butyl amine; di($C_{1-4}$) alkyl amine such as dimethyl amine, diethyl amine and dibutyl amine; tri($C_{1-4}$) alkylamine such as trimethyl amine and triethyl amine; ammonium ions such as pyridinium and hydrazinium. As the alkali metal ions, there may be mentioned, for example, lithium ion, potassium ion and sodium ion.

Examples of bivalent cations include alkali earth metal ions such as calcium ion and magnesium ion.

Among the compounds of the general formula (I) and salts thereof, sodium salt of the compound of the formula (I) wherein $R_1$ is phenyl, $R^2$ is amino, $R^3$ is chloro and X is oxygen is particularly preferable.

The compounds of the general formula (I), including the compounds of the general formula (I'), can be produced according to the following Reaction Scheme 1. That is, the pyridopyridazine compounds of the general formula (I) can be produced by a per se known method comprising reacting the compounds of the formula (II) or those of the formula (III) with hydrazine.

In the following formulas, as the lower alkyl group represented by R, R' and R", there can be mentioned alkyl groups having 1 to 6 carbon atoms such as mentioned before for $R_1$.

Reaction Scheme 1

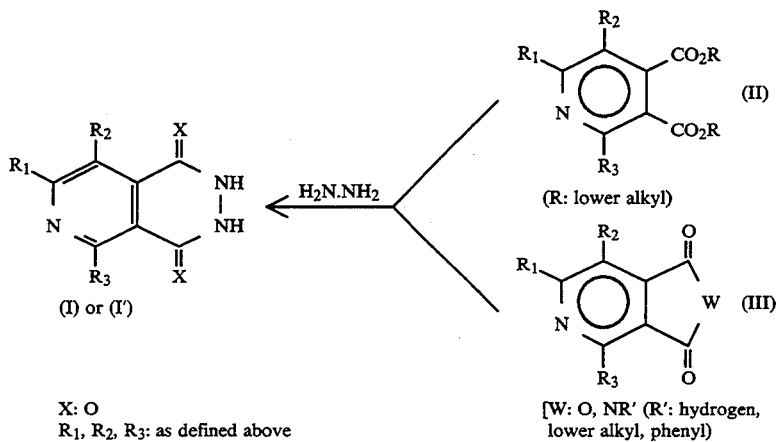

X: O
$R_1$, $R_2$, $R_3$: as defined above

[W: O, NR' (R': hydrogen, lower alkyl, phenyl)]

The compounds (II) can be obtained, for example, by subjecting 2-aminonicotinic acid ester derivatives which can be synthesized in accordance with the method by Ueno et al [Yakugaku Zassi (Pharmaceutical Journal), 82, 532(1962)], to diazotization, nitration and chlorination reactions in order, whereafter nucleophilic substitution reaction for the active chlorine atom and reduction of the nitro group are conducted, if necessary, further followed by diazotization reaction in accordance with the method by Yurugi et al. [Chem. Pharm. Bull., 24, 2699(1976)], as shown in the following Reaction Scheme 2.

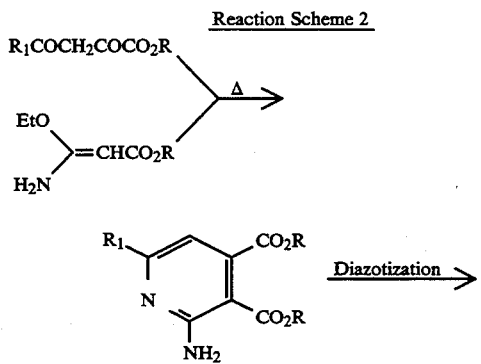

Reaction Scheme 2

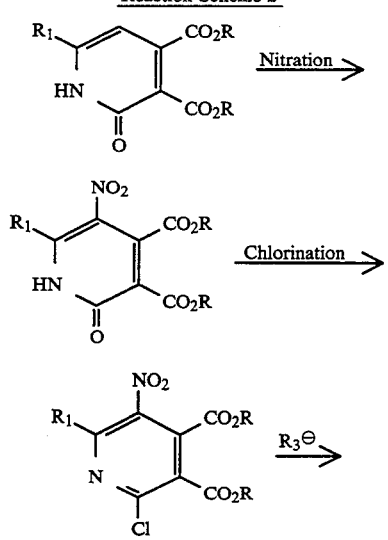

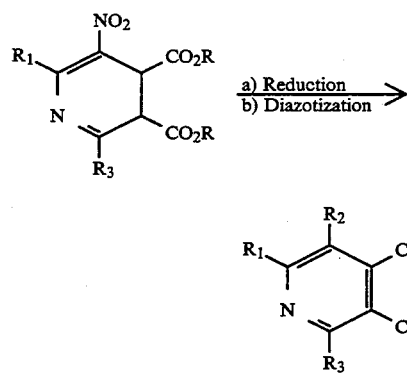

R: lower alkyl
$R_1$, $R_2$, $R_3$: as defined above

As shown below in Reaction Scheme 3, the compounds (II) and the compounds (III) can be obtained by conducting Diels-Alder reaction of the oxazole derivatives with suitable dienophiles in accordance with the method by Matsuo et al. [Yakugaku Zassi, 92, 703(1972)].

Reaction Scheme 3

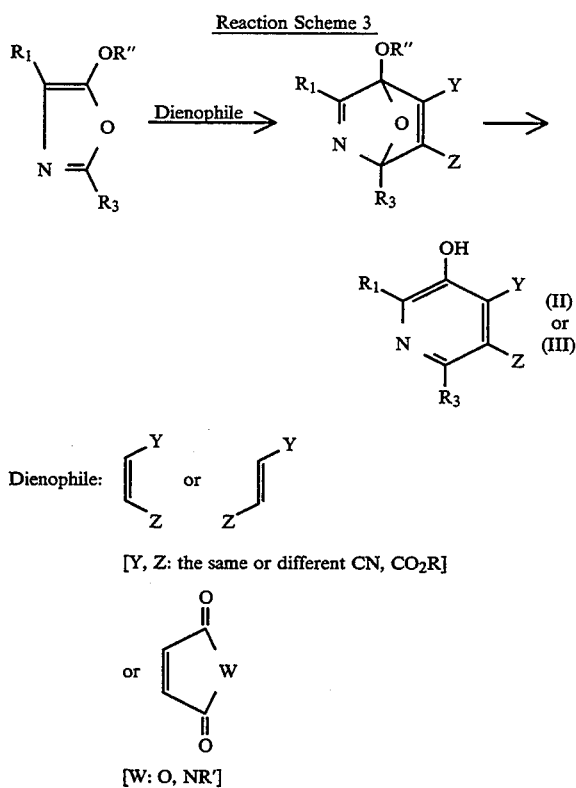

R″: lower alkyl,
R′: lower alkyl, phenyl, hydrogen atom
R : lower alkyl, $R_1$, $R_2$, $R_3$: as defined above The reaction of the compound (II) or (III) with hydrazine is usually carried out by heating without solvent or in a solvent. As the solvent, use is made of a lower alcohol such as methanol, ethanol, propanol or isopropanol; an ether such as tetrahydrofuran or dioxane; or acetic acid.

The reaction temperature is suitably in the range from 15° C. to 120° C. For the production of the compounds (II) wherein R is hydrogen atom, a hydrazine derivative such as 3,3-dimethyldiaziridine can be used in place of hydrazine.

The pyridopyridazine compounds of the general formula (I) show excellent chemiluminescent yield and thus can be utilized for various assay methods using their chemiluminescent reaction.

More specifically, for example, the following methods can be included as the advantageous methods.
(1) The pyridopyridazine compounds of the formula (I) are used as a labelling compound for antibody, hapten, antigen, nucleic acid, etc., and
(2) In enzyme immunoassay methods and nucleic acid hybridization methods in which the antibody, hapten, antigen or nucleic acid etc. is labelled with an enzyme, chemiluminescent reaction of the pyridopyridazine compounds of the general formula (I) is utilized for measurement of the enzyme activity.

In the method (1), as the first step, a pyridopyridazine compound, for example, 7-[4-(3-aminopropyloxy)-phenyl]-8-hydroxypyrido[3,4-d]pyridazine-1,4-(2H,3H)dione (hereinafter referred to also as L-011) is coupled with the substance to be labelled such as mentioned above.

The coupling can be achieved by using a per se known method. For instance, glutaraldehyde cross linking method [Immunochemistry, 6, 43 (1969); ibid. 8, 1175 (1971)], periodic acid cross linking method [J. Histochem. Cytochem., 22, 1084 (1974)], and especially the method using a coupling agent of the formula:

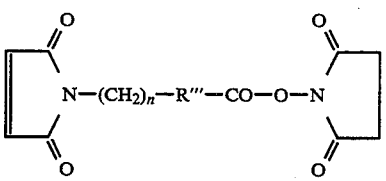

wherein, n is an integer of 0 to 5, and R‴ is a chemical bond or 6-membered cyclic hydrocarbon residue described in Japanese Patent Kokai 149,700/1983 can be preferably applied.

Furthermore, as another method for utilization, a pyridopyridazine compound is converted into its hemisuccinate with the use of succinic anhydride and further converted, with the use of N-hydroxysuccinimide and carbodiimide, into its active ester, which is coupled with the amino group of antibody, hapten, antigen, nucleic acid, etc. for labelling. Thereto, it is possible to apply coupling techniques which have been used in the relevant field. As one of the examples of assay reagents using the thus-obtained pyridopyridazine compound-labelled conjugate, mention is made of an immunochemical assay kit according to a sandwich method as shown below.

(1) The antibody immobilized on the solid phase;
(2) The antibody labelled with a pyridopyridazine compound;
(3) The standard sample of the analyte to be measured;
(4) A buffer solution to be used for dilution of the above reagents (2) and (3) and the analyte to be measured (The buffer may be any one that can be used for dilution of these reagents and sample. Examples thereof include phosphate buffers and glycine buffers of pH 6 to 9.);
(5) A buffer solution used for washing the solid phase after incubation (The buffer may be any one that can be used for washing the solid phase. Examples thereof include phosphate buffers and glycine buffers.); and
(6) A reagent necessary for evoking chemiluminescence of the pyridopyridazine compound (For example, hydrogen peroxide or microperoxidase dissolved in an alkaline solvent.)

This kit can be used, for example, in accordance with the following method.

A solution of the standard sample or a sample to be tested (about 10 to 200 μl) is diluted with the reagent (4). Each of these diluted samples was added to a mixture of a certain amount of the reagent (1) and 10–800 μl of the reagent (2), is reacted at about 0° to 40° C. for about 10 minutes to 2 days. After the reaction mixture is washed with the reagent (5), chemiluminescence of the pyridopyridazine compound bound to the solid phase is evoked. That is, immediately after addition of about 10–1000 μl of the chemiluminescent reaction reagent, the mixture is subjected to a chemiluminescence-measuring equipment for measurement of chemiluminescent quantum. In the method (2), it is necessary to prepare an enzyme-labelled conjugate by causing an enzyme in common use in the conventional enzyme immunoassay methods to be coupled, through covalent coupling, with antigen, hapten, antibody, etc.

As the method for coupling an enzyme, for example, peroxidase, with the above immunochemically active substance, a per se known method can be employed. For instance, glutaraldehyde cross linking method [Immunochemistry, 6, 43 (1969); ibid. 8, 1175 (1971)], periodic acid cross linking method [J. Histochem. Cytochem., 22, 1084 (1974)], and especially the method using a bonding agent of the formula:

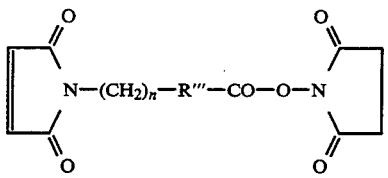

wherein, n is an integer of 0 to 5, and R''' is a chemical bond or 6-membered, cyclic hydrocarbon residue described in Japanese Patent Kokai 149,700/1983 can be preferably applied.

As one of examples of the assay reagent using the thus-obtained enzyme-labelled conjugate, mentioned below is an immunochemical assay kit according to a sandwich method.

(1) The antibody immobilized on the solid phase;
(2) The immunochemically active substance labelled with an enzyme;
(3) The standard sample of the analyte to be tested;
(4) A buffer solution to be used for dilution of the above reagents (2) and (3) and the analyte to be measured (The buffer may be any one that can be used for dilution of these reagents and sample. Examples thereof include phosphate buffers and glycine buffers of pH 6 to 9.);
(5) A buffer solution used for washing the solid phase after incubation (The buffer may be any one that can be used for washing the support. Examples thereof include phosphate buffers and glycine buffers.); and
(6) A reagent necessary for measurement of the enzyme activity [e.g. an oxidizing agent (hydrogen peroxide or its analogue, a pyridopyridazine compound and, if necessary, a chemiluminescence-enhancer]

This kit can be used, for example, in accordance with the following method.

A solution of the standard sample or a sample to be tested (about 10 to 200 μl) is diluted with the reagent (4). Each of these diluted samples was added to a mixture of a certain amount of the reagent (1) and 10–800 μl of the reagent (2), then the mixture is reacted at about 0° to 40° C. for about 10 minutes to 2 days. After the reaction mixture is washed with the reagent (5), the activity of the labelled-enzyme bound to the solid phase is measured. For example, in measuring peroxidase activity, a pyridopyridazine compound, an oxidizing agent and an enhancer are used respectively in certain amounts, and selected are the conditions under which chemiluminescent amount changes sensitively in accordance with the change in the amount even in a trace range of peroxidase. It is known that in chemiluminescent reaction, employment of an enhancer brings about delay of luminous reaction and increase in luminous amount [Thorpe et al., Anal. Biochem. 145, 96 (1985)]; Methods in Enzymology edited by M. A. DeLuca, 1986, 331, published by Academic Press].

The chemiluminescent reaction is preferably carried out usually under the following conditions.

The reaction temperature may be 0° to 60° C., preferably 5° to 30° C. The pH value of a buffer to be used may be within the range from around neutral to alkaline, for instance, pH 7 to 10, preferably pH 7.5 to 9. Various kinds of buffers can be used as the buffer, and among others, borate buffer, phosphate buffer, carbonate buffer, Tris buffer, etc. can be preferably used.

While the concentrations of the reagents to be used can vary in accordance with the species of the enhancer to be used, in general, the following concentrations are preferable:

| | |
|---|---|
| (a) oxidizing agent (hydrogen peroxide) | 1 μM–30 mM |
| (b) enhancer | 0.1 μM–10 mM |
| (c) a pyridopyridazine compound | 1 μM–10 mM |

Particularly, preferred are the concentrations of 20 μM–2 mM for (a), 4 μM–1 mM for (b) and 10 μM–2 mM for (c).

The chemiluminescent reaction is evoked by adding (a)–(c) to the peroxidase combined on the solid phase.

The luminous quantum produced in the reaction solution can be measured by a measuring instrument which is marketed or one's own making (e.g., a photocounter equipped with a high sensitive photonmultiplier). That is, a quantitative analysis can be conducted by measuring luminous quantum during the period of few seconds to few minutes at the stage of few seconds to several tens of minutes after the addition of the last solution.

Namely, a reliable relationship between the luminous quantum actually measured and the amount of the peroxidase can be recognized, based on which the analysis is possible.

As another type of method, mention is made of a method which comprises producing hydrogen peroxide in accordance with the amount of the enzyme by reacting glucose with glucoseoxidase bound onto the solid phase, followed by chemiluminescence of a pyridopyridazine compound with the use of, for example, microperoxidase as a reaction catalyst.

The luminous quantum produced in the reaction solution can be measured by a measuring instrument which is marketed or one's own making (e.g., a photocounter equipped with a high sensitive photonmultiplier). That is, a quantitative analysis can be conducted by measuring luminous quantum during the period of few seconds to few minutes at the stage of few seconds to several tens of minutes after the addition of the last solution.

Namely, a reliable relationship between the luminous quantum actually measured and the amount of the glucoseoxidase can be recognized, based on which the analysis is possible.

As a further different type of method, a system utilizing liposome provides an effective measuring means.

In a liposome prepared artificially are incorporated, for example, (a) a pyridopyridazine compound or (b) a substance acting as a catalyst for chemiluminescent reaction, for instance, a catalyst such as peroxidase, microperoxidase, a compound having a porphin structure, etc., and onto the surface of the liposome is immobilized an immunochemically active substance such as antigen, antibody, hapten, etc., through covalent bond. Liposome can be prepared by a per se known methods.

For instance, liposome can be prepared from a mixture of cholesterol, lecithin, phosphatidic acid and a small amount of labelling ingredient (e.g. dithiopyridylphosphatidyl ethanolamine). By a per se known method, assay is carried out, and at the step of measurement-reading, by adding a complement or a substance capable of breaking the liposome membrane (an acid, a base, a salt, etc.), the substances incorporated inside are allowed to migrate to the solution. In the case of (a), for example, if necessary, in the presence an oxidizing agent and a catalyst (peroxidase, microperoxidase, a porphin structure-containing compound), chemiluminescence of a pyridopyridazine compound is evoked. In the case of (b), for example, if necessary, in the presence of an oxidizing agent, chemiluminescence of a pyridopyridazine compound can be evoked. In said chemiluminescence, a suitable chemiluminescent enhancer may be used.

The luminous quantum produced in the reaction solution can be measured by a measuring instrument which is marketed or one's own making (e.g., a photocounter equipped with a high sensitive photonmultiplier). That is, a quantitative analysis can be conducted by measuring luminous quantum during the period of few seconds to few minutes at the stage of few seconds to several tens of minutes after the addition of the last solution.

Namely, a reliable relationship between the luminous quantum actually measured and the amount of the glucoseoxidase can be recognized, based on which the analysis is possible.

By the foregoing assay method of the present invention utilizing chemiluminescence of a pyridopyridazine compound of the formula (I), it is possible to measure a substance existing in a trace amount in a liquid sample. Particularly, useful are the assay method which comprises measuring a substance existing in a trace amount in a liquid sample by adding a pyridopyridazine compound of the formula (I) and, if desired, a catalyst to a system which is capable of producing hydrogen peroxide in an assay system, to evoke chemiluminescent reaction, in such a manner as mentioned above. Examples of the substance existing in a trace amount include acidic or basic fibroblast growth factor (hereinafter sometimes referred to respectively as aFGF and bFGF), nerve growth factor (hereinafter referred to as NGF) and endothelin.

Furthermore, it is expected that by the high sensitive assay method of the present invention, relationship between increase or decrease of such substances existing in a trace amount in diseases (e.g. relationship between FGF and tumors, that between NGF and nervous diseases, that between endothelin and cardiovascular diseases) can be made clear. Ultimately, provided are the methods for diagnosing such diseases as mentioned above by the assay methods of the present invention. Thus, the diagnosis of the diseases at the earlier stage thereof is enabled. As the preferred embodiments, there can be mentioned methods for diagnosing tumors including cancers by measuring bFGF, especially bFGF in serum, as illustrated sepcifically in the below-described Example 28.

Figure 1:
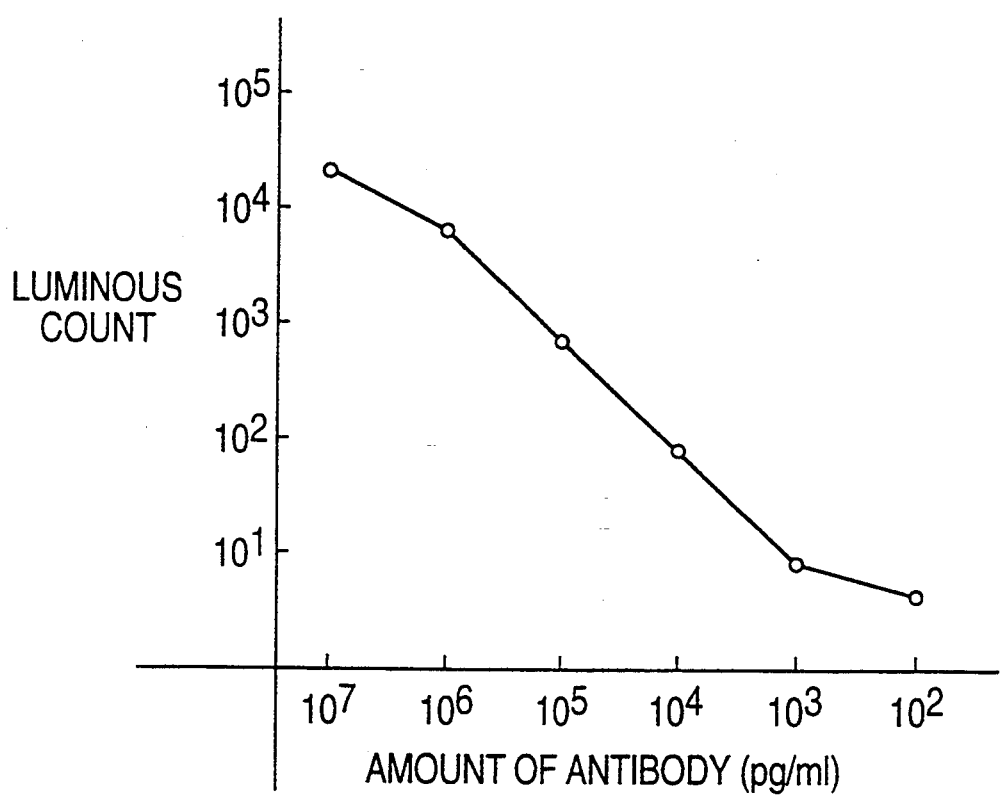
FIG. 1 is the graph showing relationship between the amount of the anti-interferon γ antibody labelled with the compound (L-011) of Example 2 and the luminous count.

Below, this invention is described in further detail by illustrating reference examples and working examples, which are not limitative on the scope of the present invention.

REFERENCE EXAMPLE 1

Phenylglycine ethyl ester hydrochloride

D-phenylglycine (30.0 g) was suspended in 500 ml of ethanol, and hydrogen chloride gas (about 250 g) was bubbled into the suspension under ice-cooling. The mixture was left standing at room temperature overnight. The solvent was distilled off, and the resulting crystals were collected by filtration with diethyl ether, Yield: 27.7 g(64.7%). NMR(CDCl$_3$) δ(ppm): 1.13(3H,t,J=7.2 Hz), 4.12(2H,q,J=7.2 Hz), 5.13(1H,s), 5.42(5H,m), 9.17(3H,br.). IR(KBr)ν: 2980–2900, 1755, 1738, 1495, 1235, 700 cm$^{-1}$.

REFERENCE EXAMPLE 2

N-Formylphenylglycine ethyl ester

Phenylglycine ethyl ester hydrochloride (21.5 g; 0.1 mol) was dissolved in 200 ml of formic acid, whereto sodium formate (8.16 g; 1.2 eq.) was added, followed by adding dropwise acetic anhydride (20 ml; 2.1 eq.). After two hours' stirring, 10 ml of acetic anhydride was added dropwise, and the mixture was stirred at 50°–60° C. for 1.5 hours. After the solvent was distilled off, the residue was neutralized with an aqueous solution of sodium hydrogencarbonate and extracted with ethyl acetate. The organic layer was washed with a saturated aqueous solution of sodium chloride and dried over magnesium sulfate. The solvent was distilled off to afford an oily product.

Yield: 22.7 g. NMR(CDCl$_3$)δ: 1.20(3H,t,J=7.2 Hz), 4.18(2H,dq,J=2.4,7.2 Hz), 5.63(1H,d,J=7.5 Hz), 6.78(1H,br.), 7.33(5H,s), 8.22(1H,s). IR(neat)ν: 2980, 1640, 1520, 1495, 1380, 1350, 1015 cm$^{-1}$.

REFERENCE EXAMPLE 3

5-Ethoxy-4-phenyloxazole

A mixture of phosphorus pentoxide (32 g; 2.1 eq.), Hyflo Super-Cel® [Jone's-Manville Sales Corp.] (9 g) and dichloroethane (120 ml) was vigorously stirred at 50°–60° C., and 22.7 g of N-formylphenylglycine ethyl ester was added dropwise over 40 minutes. After 30 ml of dichloroethane was added, the mixture was stirred for 8 hours. Sodium hydrogencarbonate (80 g/water 100 ml) was added for neutralization, followed by filtration to give the organic layer. The aqueous layer was extracted with dichloromethane. The organic layers were combined, and dried over magnesium sulfate. Thereafter, the solvent was distilled off, and the residue was subjected to silica gel column chromatography(eluent: dichloromethane/hexane 1:1) for purification, thereby to obtain a red oily substance.

Yield: 9.7 g (46.8%). NMR(CDCl$_3$)δ(ppm): 1.44(3H,t,J=6.9 Hz), 4.33(2H,q,J=6.9 Hz), 7.23(3H,m), 7.49(1H,s), 7.82(2H,d,J=6.9 Hz). IR(neat)ν: 2980, 1640, 1520, 1495, 1380, 1350, 1015 cm$^{-1}$.

REFERENCE EXAMPLE 4 trans-3,6-Epoxy-3-ethoxy-4,5-dimethoxycarbonyl-2-phenyl-3,4,5,6-tetrahydropyridine.

Dimethyl fumarate (8.13 g; 1.1 eq.) was added to 5-ethoxy-4-phenyloxazole (9.7 g; 51.3 mmol), and the mixture was reacted at 120° C. Two hours' later, dimethyl fumarate (2.2 g; 0.3 eq.) was further added, and the mixture was stirred for further 1.5 hours. The reaction mixture was purified by silica gel column chromatography (eluent: dichloromethane), to give crude crystals. The crude crystals were recrystallized from dichloromethane/hexane to give colorless needles.

Yield: 6.53 g (38.2%). m.p. 98.5°-99.5° C. NMR(CDCl$_3$)δ(ppm): 1.33(3H,t,J=6.9 Hz), 3.30(1H,d,J=4.2 Hz ), 3.40(3H,s ) , 3.62(1H,d,J=4.2 Hz ), 3.78(3H,s), 3.90(2H,m), 6.04(1H,s), 7.40(2H,m) , 7.43(1H,m), 7.99(2H,m). IR(KBr)ν: 1725, 1 310, 1295, I200, 1170, 985 cm$^{-1}$. Elemental Analysis Calcd. C:61.25; H:5.75; N:4.20. Found C:61.07; H:5.75; N:4.05.

REFERENCE EXAMPLE 5

8-Hydroxy-7-phenylpyrido[3,4-d]pyridazine-1, 4(2H, 3H)-dione (L-002).

3,6-Epoxy-3-ethoxy-4,5-dimethoxycarbonyl-2-phenyl-3,4,5,6-tetrahydropyridine (500 mg; 1.5 mmol) was added to hydrazine monohydrate (5 ml), and the mixture was heated in a stream of nitrogen at 100° C. for 1 hour. Under ice-cooling, water was added to reaction mixture, and the mixture was neutralized with acetic acid. The resulting yellow crystalline precipitate was recovered by filtration. Yield: 210 mg (55.0%).

m.p. >300° C. NMR(DMSO-d$_6$) δ(ppm): 7.41(3H,m), 8.17(2H,m), 8.73(1H,s). IR(KBr)ν: 3420, 3175, 3050, 1650, 1580 cm$^{-1}$.

REFERENCE EXAMPLE 6

N-Boc-p-hydroxyphenylglycine.

To 33.4 g (0.2 mol) of p-hydroxyphenylglycine were added 110 ml of water, 42 ml (1.5 eq.) of triethylamine, 52.8 g (1.1 eq.) of S-t-butoxycarbonyl-4,6-dimethyl-2-mercaptopyrimidine and 110 ml of dioxane, and the mixture was stirred at room temperature for 14 hours. To the reaction mixture was added 300 ml of water, and the mixture was extracted with 400 ml of ethyl acetate. The organic layer was extracted with 100 ml of a 5% aqueous solution of sodium hydrogencarbonate. The aqueous layers were combined, adjusted to pH 3 with 5N hydrochloric acid under ice-cooling and extracted with ethyl acetate. The organic layer was washed with an aqueous solution of potassium hydrogensulfate and a saturated aqueous solution of sodium chloride, and dried over magnesium sulfate. The solvent was distilled off. The thus-obtained crystals were collected by filtration with ethyl acetate/hexane. Yield: 46.0 g (86.1%).

NMR (DMSO-d$_6$)δ(ppm): 1.38 (9H,s), 4.92 (1H,d,J=7.8 Hz),6.67 (2H,d,J=8.4 Hz), 7.13(2H,d,J=8.4 Hz).

REFERENCE EXAMPLE 7

N-Boc-p-methoxyphenylglycine methyl ester

In 200 ml of methanol was dissolved 8.3 g (2.2 eq.) of sodium. After the solution was ice-cooled, 46.0 g of N-Boc-p-hydoxyphenylglycine was added, followed by dropwise addition of 23.6 ml (2.2 eq.) of iodomethane. The mixture was left standing for 2 days at room temperature. Thereafter, 23.6 ml of iodomethane was added dropwise, and the mixture was heated at 40°-50° C. for 5 hours. After 2 hours' heating under reflux, the solvent was distilled off. To the residue were added 100 ml of DMF and 20 ml of iodomethane, and the mixture was heated to 40°-50° C. After iodomethane was removed, 500 ml of ice-water was added and the mixture was extracted with ethyl acetate. The organic layer washed with water, and a saturated aqueous solution of sodium chloride, and dried over magnesium sulfate. The solvent was distilled, and the residue was purified by silica gel column chromatography (eluent: ethyl acetate/hexane 1:1), thereby to give colorless needles. Yield:37.0 g (72.7%).

NMR(CDCl$_3$)δ(ppm): 1.43(9H,s), 3.71(3H,s), 3.80(3H,s), 5.22(1H,d,J=7.5 Hz), 5.45(1H,br.), 6.87(2H,d,J=6.0 Hz), 7.28(2H,d, J=6.0 Hz).

REFERENCE EXAMPLE 8

N-Formyl-p-methoxyphenylglycine methyl ester

In 250 ml of formic acid was dissolved 36.9 g of N-Boc-p-methoxyphenylglycine methyl ester, and the mixture was stirred at room temperature for 3 hours and subsequently at 40°-50° C. for 1 hour. After dropwise addition of 24.8 ml (2.1 eq.) of acetic anhydride, the mixture was stirred at room temperature overnight and 40°-50° C. for 2 hours. After the solvent was distilled off, the residue was neutralized with an aqueous solution of sodium hydrogencarbonate, followed by extraction with ethyl acetate. The organic layer was washed with water and a saturated aqueous solution of sodium chloride and dried over magnesium sulfate. The solvent was distilled off. The crystals were collected by filtration with hexane.

Yield: 24 g(86.1%). m.p. 97°-99° C. NMR(CDCl$_3$)δ(ppm): 3.73(3H,s), 3.79(3H,s), 5.57(1H,d,J=7.5 Hz), 6.60(1H,br.), 6.87(2H,d,J=8.7 Hz), 7.28(2H,d,J=8.7 Hz), 8.22(1H,s),1R(KBr)ν: 3340, 1745, 1670, 1515,1320, 1180 cm$^{-1}$.

REFERENCE EXAMPLE 9

5-Ethoxyoxazole

A mixture of phosphorus pentoxide(30 g;2.1 eq.), Hyflo Super-Cel ® (17.5 g) and dichloroethane(175 ml) was vigorously stirred at 60°-70° C., and then 12.86 g of N-formylglycine ethyl ester was added dropwise over 50 minutes. The mixture was stirred for 8 hours. Under ice-cooling, sodium hydrogencarbonate (100 g/water 100 ml) was added for neutralization. The mixture was filtered to give an organic layer. The aqueous layer was extracted with dichloromethane. The organic layers were combined and dried over magnesium sulfate. Thereafter, the solvent was distilled off. The residue was purified by silica gel column chromatography (eluent: ethyl acetate/hexane 1:2), thereby to give an oily substance. Yield: 560 mg (5%).

(CDCl$_3$)δ(ppm): 1.42(3H,t,J=7.2 Hz),4.13(2H,q,J=7.2 Hz), 6.11(1H,s), 7.33(1H,s).

REFERENCE EXAMPLE 10

3,4-Dimethoxycarbonyl-5-hydroxypyridine.

Dimethyl fumarate (781 mg; 1.1 eq.) was added to 5-ethoxyoxazole (557.3 mg; 4.9 mmol), and the mixture was reacted at 120° C. for 1.5 hours. The reaction residue was purified by silica gel column chromatography (eluent: ethyl acetate/hexane 2:1), to give crude crystals of the title compound. Yield: 730 mg (70.2%). The crude crystals were recrystallized from dichloromethane-hexane, to give colorless plates.

m.p. 136°-137° C. NMR(CDCl$_3$)δ(ppm): 3.91 (3H,s), 3.95 (3H,s), 8.28(1H,s), 8.54(1H,s), 9.92(1H,s). IR(KBr)ν: 1745, 1730, 1435, 1320, 1300, 1285 cm$^{-1}$.

REFERENCE EXAMPLE 11

3-Amino-4,5-diethoxycarbonyl-2-phenylpyridine

A mixture of 100 mg of 3-amino-6-chloro-4,5-diethoxycarbonyl-2-phenylpyridine, 0.08 ml (2.0 eq.) of triethylamine amd 8 ml of ethyl acetate was subjected to catalytic reduction for 7 hours with 100 mg of 10% Pd-C (50% wet). The catalyst was removed by filtration, and the solvent was distilled off. Yield: 86 mg(95.4%).

NMR(CDCl$_3$)δ(ppm)(ppm): 1.37(3H,t,J=7.2 Hz), 1.39(3H,t,J=7.2 Hz), 4.38(4H,q,J=7.2 Hz), 5.17(2H,s), 7.48-7.65(5H,m), 8.33(1H,s). IR(neat)ν: 3475, 3355, 2975, 1720, 1600, 1405, 1280, 1240 cm$^{-1}$.

REFERENCE EXAMPLE 12

8-Amino-7-phenylpyrido[3,4-d]pyridazine-1,4-(2H,3H)-dione (L-010)

To 200 mg of 3-amino-4,5-diethoxycarbonyl-2-phenylpyridine was added 2 ml of hydrazine monohydrate, and the mixture was heated in a stream of nitrogen gas at 100° C. for 1 hour.

Under ice-cooling, water was added to the reaction mixture, and the mixture was neutralized with hydrochloric acid and adjusted to pH 5. The resulting yellow crystalline precipitate was collected by filtration, Yield: 93 mg (57.5%). m.p. >300° C.

NMR(DMSO-d$_6$)δ(ppm): 7.19(2H,s), 7.48-7.71(5H,m), 8.39(1H,s). IR(KBr)ν: 3430, 1640 cm$^{-1}$.

REFERENCE EXAMPLE 13

Ethyl benzoylpyruvate

In 560 ml of ethanol was dissolved 25 g (1.08 eq.) of sodium and a mixture of 135.6ml (146 g; 1 mol) of diethyl oxalate and 116.7 ml (120 g; 1 mol) of acetophenone was added thereto dropwise at 40° C. One hour later, reflux was begun and it was continued for 30 minutes. The solvent was distilled off. The residue was neutralized with sulfuric acid (55 g/water 200 ml), and the mixture was extracted with ethyl acetate. The organic layer was washed with water and a saturated aqueous solution of sodium chloride, and dried over magnesium sulfate. Thereafter, the solvent was distilled off, and the residue was purified by silica gel column chromatography (eluent: dichloromethane/hexane 1:1), to give colorless plates. The crystals were recovered by filtration with ethyl acetate/hexane. Yield: 114.6 g. (52.0%). NMR(CDCl$_3$)δ(ppm): 1.42(3H,t,J=7.0 Hz), 4.40(2H,d,J=7.0 Hz), 7.08(1H,s), 7.57(3H,m), 8.02(2H,dd,J=2.1, 7.5 Hz).

REFERENCE EXAMPLE 14

Ethyl 3-amino-3-ethoxyacrylate.

Under ice-cooling, 93.5 g (1.3 eq.) of hydrogen chloride gas was bubbled into a mixture of 226 g (2 mol) of ethyl cyanoacetate, 101 g (2.2 mol) of ethanol and 100 g of dried diethyl ether, and the mixture was left standing overnight. The resulting colorless prisms (hydrochloride) were collected by filtration with diethyl ether. Yield: 352.5 g. m.p.103°-105° C.

NMR ( DMSO-d$_6$)δ(ppm): 1.23( 3H,t,J=7.2 Hz), 1.37 (3H,t,J=7.2 Hz ), 3.94 (2H,br.), 4.15 ( 2H,q,J=7.2 Hz ), 4.51 (2H,q,J=6.8 Hz).

The thus-obtained crystals were added to an ice-cooled aqueous solution of 200 g (1.2 eq.) of sodium hydrogencarbonate and the mixture was extracted with diethyl ether. The organic layer was washed with water and a saturated aqueous solution of sodium chloride and dried over magnesium sulfate. Thereafter, the solvent was distilled off, and the residue was purified by distillation under reduced pressure. Yield: 253.8 g (79.7%). b.p.$_{1.8}$ 78° C. IR(neat)ν: 2980, 1660, 1610, 1540, 1160, 1070 cm$^{-1}$.

REFERENCE EXAMPLE 15

2-Amino-3,4-diethoxycarbonyl-6-phenylpyridine hydrochloride.

A mixture of 1.11 g (5 mmol) of ethyl benzoylpyruvate and 1.75 g (2.2 eq.) of ethyl 3-amino-3-ethoxyacrylate was heated at 100° C. for 1.5 hours. The low boiling substances were distilled off under reduced pressure. Thereafter, 2 ml of 10% hydrochloric acid was added to the reaction mixture, and the resulting crystals were collected by filtration with diethyl ether. The crystals were recrystallized from ethyl acetate, to give pale yellow needles. Yield: 0.7 g(39.8%). m.p.78-81, 145°-148° C.(double m.p.).

NMR(CDCl$_3$)δ(ppm): 1.26(3H,t,J=7.5 Hz), 1.30(3H,t,J=7.5 Hz), 4.27(2H,q,J=7.5 Hz), 4.28(2H,q,J=7.5 Hz), 7.17( 1H,s), 7.43(3H,m), 8.05(2H,m). IR(KBr)ν: 1740, 1700, 1650, 1300 cm$^{-1}$. Elemental Analysis: Calcd. (C$_{17}$H$_{18}$N$_2$O$_4$. HCl)C: 58.21; H:5.46; N:7.99. Found C:58.45; H:5.48; N:8.04.

REFERENCE EXAMPLE 16

3,4-Diethoxycarbonyl-6-phenyl-2-pyridone.

In a mixture of 90 ml of 2% hydrochloric acid and 60 ml of dioxane was dissolved 3.50 g (10 mmol) of 2-amino-3,4-diethoxycarbonyl-6-phenylpyridine hydrochloride. A solution of 0.83 g (1.2 eq.) of sodium nitrite dissolved in 3 ml of water was added dropwise thereto. The mixture was stirred at room temperature for 4 hours and left standing overnight. The solvent was distilled off. The resulting crystals were collected by filtration with water. The crystals were recrystallized from ethanol, to give pale yellow prisms.

Yield: 1.9 g (60.3%). m.p.143°-144° C. NMR(CDCl$_3$)δ(ppm): 1.33(3H,t,J=7.2 Hz), 1.36(3H,t,J=7.2 Hz), 4.37(4H,q,J=7.2 Hz), 6.95(1H,s), 7.47(3H,m), 7.79(2H,m). IR(KBr)ν: 2900-3000, 1740, 1635, 1615, 1245 cm$^{-1}$. Elemental Analysis: Calcd. (C$_{17}$H$_{17}$NO$_5$) C:64.75; H:5.43; N:4.44. Found C:64.82; H:5.55; N:4.46.

REFERENCE EXAMPLE 17

3,4-Diethoxycarbonyl-5-nitro-6-phenyl-2-pyridone.

In 13 ml of acetic anhydride was suspended 5.0 g of 3,4-diethoxycarbonyl-6-phenyl-2-pyridone; and the suspension was cooled to −10° C. Fuming nitric acid (1.32 ml; 2.0 eq.) was added dropwise over 1 hour, and the mixture was stirred for 45 minutes as it is. After 40 ml of water was added, the mixture was stirred at room temperature and left standing overnight. The resulting crystals were collected by filtration and dried. Yield: 4.61 g (80.7%). The crystals were recrystallized from ethanol, to give pale yellow needles.

m.p. 172°–173° C. NMR(CDCl$_3$)δ(ppm): 1.37(3H,t,J=7.1 Hz), 1.38(3H,t,J=7.1 Hz), 4.40(2H,q,J=7.1 Hz), 4.42(2H,q,J=7.1 Hz), 7.52(5H,m). 1R(KBr)ν: 3450, 1740, 1650, 1525, 1345, 1285 cm$^{-1}$. Elemental Analysis: Calcd. (C$_{17}$H$_{16}$N$_2$O$_7$)C: 56.67; H:4.48; N:7.77. Found C:56.96; H:4.56; N:7.60.

REFERENCE EXAMPLE 18

2-Chloro-3,4-diethoxycarbonyl-5-nitro-6-phenylpyridine

To 1.0 g of 3,4-diethoxycarbonyl-5-nitro-6-phenyl-2-pyridone was added 1.3 ml (3.37 eq.) of phenylphosphonic dichloride, and the mixture was heated at 150° C. for 2.5 hours. Water was added to the reaction mixture, and the mixture was extracted with ethyl acetate. The organic layer was washed with water and a saturated aqueous solution of sodium chloride, and dried over magnesium sulfate. The solvent was distilled off, and the residue was purified by silica gel column chromatography (eluent: ethyl acetate/hexane 1:2), to give an oily product. Yield: 950 mg (90.5%).

NMR(CDCl$_3$)δ(ppm): 1.35(3H,t,J=7.2 Hz), 1.42(3H,t,J=7.2 Hz), 4.44(4H,q,J=7.2 Hz), 7.52 (5H,m). 1R(KBr)ν: 2990, 1750, 1580, 1550 cm$^{-1}$.

REFERENCE EXAMPLE 19

3-Amino-6-chloro-4,5-diethoxycarbonyl-2-phenylpyridine

A mixture of 400 mg 2-chloro-3,4-diethoxy carbonyl-5-nitro-6-phenylpyridine, 520 mg of reduced iron and 4 ml of ethanol was heated to 60° C., and 2.3 ml of conc. hydrochloric acid was added dropwise over 30 minutes. Under ice-cooling, the mixture was neutralized with a saturated aqueous solution 0f sodium hydrogencarbonate and extracted with dichloromethane. The organic layer dried, and thereafter, the solvent was distilled off, to give crystals. Yield: 337 mg(91.5%). The crystals were recrystallized from dichloromethanehexane, to give pale yellow prisms.

m.p. 93°–94° C. NMR(CDCl$_3$)δ(ppm): 1.37(3H,t,J=7.0 Hz), 1.43(3H,t,J=7.0 Hz), 4.37 (2H,q,J=7.0 Hz), 4.43(2H,q,J=7.0 Hz), 5.93(2H,m), 7.48–7.57(5H,m). 1R(KBr)ν: 3510, 3400, 1760, 1725, 1615, 1265 cm$^{-1}$. Elemental Analysis: Calcd. (C$_{17}$H$_{17}$N$_2$O$_4$Cl)C: 58.54; H4.91; N:8.03. Found C: 58.47; H:4.87; N:7.97.

REFERENCE EXAMPLE 20

5-methoxy-4-(p-methoxyphenyl)oxazole.

A mixture of phosphorus pentoxide (30 g; 2.1 eq.), Hyflo Super-Cel® (17.5 g) and dichloroethane (150 ml) was vigorously stirred at 50°–60° C., whereto 22.3 g (0.1 mol) of N-formyl-p-methoxyphenylglycine methyl ester as obtained in Reference Example 8 dissolved in 50 ml of dichloromethane was added dropwise. The mixture was stirred overnight. Under ice-cooling, the reaction mixture was neutralized by adding sodium hydrogencarbonate (100 g/water 100 ml). The mixture was filtered to obtain an organic layer. The aqueous layer was extracted with dichloromethane. The organic layers were combined, and dried over magnesium sulfate. The solvent was distilled off. The residue was purified by silica gel column chromatography (eluent: ethyl acetate/hexane 1:2), to give pale yellow needles. Yield: 10.2 g (49.8%).

NMR(CDCl$_3$)δ(ppm): 3.82(3H,s), 4.03(3H,s), 6.92(2H,d,J=8.7 Hz), 7.44(1H,s), 7.72(2H,d,J=8.7 Hz).

REFERENCE EXAMPLE 21 cis-3,6-Epoxy-4,5-dimethoxycarbonyl-3-methoxy-2-(p-methoxyphenyl)-3,4,5,6-tetrahydropyridine.

A mixture of 200 mg of 5-methoxy-4-(p-methoxyphenyl)oxazole and 157 mg (1.1 eq.) of dimethyl maleate was heated at 120° C. for 1.5 hours. The product was purified by silica gel column chromatography (eluent: ethyl acetate/hexane 1:1). Exo form: colorless plates Yield: 130 mg. m.p. 148°–150° C.

NMR(CDCl$_3$)δ(ppm): 3.04(2H,s), 3.50(3H,s), 3.72(3H,s), 3.74(3H,s), 3.85(3H,s), 6.24(1H,s), 6.98(2H,d,J=8.7 Hz), 7.96(2H,d,J=8.7 Hz). Endo form: colorless prisms. Yield: 40 mg(11.8%). NMR(CDCl$_3$)δ(ppm): 3.49(3H,s), 3.57(3H,s), 3.65(3H,s), 3.83(2H,m), 3.86(3H,s), 5.99(1H,d,J=3.6 Hz), 6.92(2H,d,J=9 Hz), 8.04(2H,d,J=9 Hz).

EXAMPLE 1

8-Hydroxy-7-(p-methoxyphenyl)pyrido[3,4-d]-pyridazine-1,4(2H,3H)dione (L-003).

To 1.0 g of cis-3.6-epoxy-4,5-dimethoxycarbonyl-3-methoxy-2-(p-methoxyphenyl)-3,4,5,6-tetrahydropyridine (exo form) was added 10 ml of hydrazine monohydrate, and the mixture was heated at 100° C. in a stream of nitrogen for 1 hour. Under ice-cooling, water was added to the reaction mixture, and the mixture was neutralized with acetic acid and adjusted to pH 3. The resulting yellow crystalline precipitate was collected by filtration. The crystals were dissolved in 1N-sodium hydroxide and the solution was purified by Sephadex ® LH-20 column chromatography (eluent: water). The product was lyophilized.

Yield: 190 mg(18.4%). NMR(DMSO-d$_6$)δ(ppm): 3.80(3H,s), 6.96(2H,d,J=9.0 Hz), 8.33(1H,s), 8.45(2H,d,J=9.0 Hz). IR(KBr)ν:1660, 1610, 1585, 1365, 1255 cm$^{-1}$. Elemental Analysis:Calcd.(C$_{14}$H$_{10}$N$_3$O$_4$-Na.3H$_2$O) C:46.54; H:4.46; N:11.63. Found C:46.75; H:4.40, N:11.64.

REFERENCE EXAMPLE 22

N-Boc-4-(3-phthalimidopropyloxy)phenylglycine methyl ester

To 10 ml of anhydrous DMF were added 2.8 g of N-Boc-p-hydroxyphenylglycine methyl ester and 1.38 g (1.0 eq) of anhydrous potassium carbonate, followed by addition of 2.68 g (1.0 eq.) of N-(3-bromopropyl)phthalimide. The mixture was heated at 100° C. for 1 hour. The reaction mixture was poured into ice water, and the mixture was extracted with ethyl acetate. The organic layer was washed with water and a saturated aqueous solution of sodium chloride, and dried. Thereafter, the solvent was distilled off. The residue was purified by silica gel column chromatography (eluent: 5% ethyl acetate/dichloromethane), to give colorless crystals.

Yield: 3.88 g (82.6%). NMR(CDCl$_3$)δ(ppm): 1.43(9H,s), 2.18(2H,m), 3.71(3H,s), 3.91(2H,t,J=6.8 Hz), 4.02(2H,t,J=6.0 Hz), 5.23(1H,d,J=6.3 Hz), 5.46(1H,d,J=6.3 Hz), 6.78(2H,d,J=8.8 Hz), 7.23(2H,d,J=8.8 Hz), 7.73(2H,m), 7.85(2H,m)

REFERENCE EXAMPLE 23

N-Formyl-4-(3-phthalaimidopropyloxy)phenylglycine methyl ester

To 3.0 g of N-Boc-4-(3-phthalimidopropyloxy)phenylglycine methyl ester was added 25 ml of formic acid, and the mixture was stirred at 40°–50° C. for 30 minutes. Thereto was added dropwise 1.27 ml (2.1 eq.) of acetic anhydride under ice-cooling, and the mixture was stirred overnight. After 1 ml of acetic anhydride was added, the mixture was stirred at 40°–50° C. for 2 hours. After the solvent was distilled off, the residue was neutralized with an aqueous solution of sodium hydrogencarbonate, which was followed by extraction with ethyl acetate. The organic layer was washed with water and a saturated aqueous solution of sodium chloride and thereafter dried. The solvent was distilled off. The resulting colorless crystals were collected by filtration with hexane.

Yield: 2.43 g (95.7%). NMR(CDCl$_3$)δ(ppm): 2.18(2H,m), 3.74(3H,s), 3.90(2H,t,J=6.9 Hz), 4.01(2H,t,J=6.0 Hz), 5.57(1H,d,J=7.4 Hz), 5.58(1H,d,J=7.4 Hz), 6.78(2H,d,J=8.8 Hz), 7.23(2H,d,J=8.8 Hz), 7.71(2H,m), 7.85(2H,m), 8.21(1H,s).

REFERENCE EXAMPLE 24

5-Methoxy-4-[4-(3-phthalimidopropyloxy)phenyl]oxazole

A mixture of 0.75 g of Hyflo Super-Cel ® and 1.5 g of phosphorus pentoxide with 15 ml of dichloroethane was heated to 50°–60° C. and vigorously stirred. Thereto was added dropwise 2.0 g of N-formyl-4-(3-phthalimidopropyloxy)phenylglycine methyl ester dissolved in 20 ml of dichloroethane. The mixture was stirred overnight. Under ice-cooling, the reaction mixture was neutralized with a saturated aqueous solution of sodium hydrogencarbonate, and filtered with Hyflo Super-Cel ®, followed by fractional extraction. The aqueous layer was extracted with dichloromethane, and the organic layers were combined, washed and dried. The solvent was distilled off. The resulting crystals were collected by filtration with ethyl acetate/hexane.

Yield: 0.88 g (46.1%). NMR(CDCl$_3$)δ(ppm): 2.20(2H,m), 3.93(2H,t,J=7.0 Hz), 4.05(3H,s), 4.06(2H,t,J=6.0 Hz), 6.84(2H,d,J=8.8 Hz), 7.47(1H,s), 7.69(2H,d,J=8.8 Hz), 7.70(2H,m), 7.86(2H,m).

REFERENCE EXAMPLE 25 cis-3.6-Epoxy-3-methoxy-4,5-dimethoxycarbonyl-2-[4-(3-phthalimidopropyloxy)phenyl]-3,4,5,6-tetrahydropyridine To 120 mg of 5-methyoxy-4-[4-(3-phthalimidopropyloxy)phenyl]oxazole was added 0.5 g (10 eq.) of dimethyl maleate, and the mixture was heated at 120° C. for 3 hours. The residue was purified by silica gel column chromatography (eluent:ethyl acetate/hexane 1:2).

Exo adduct of the title compound: yield: 75 mg (45.4%). NMR (CDCl$_3$)δ(ppm): 2.23(2H,m), 3.05(1H,s), 3.06 (1H,s), 3.50(3H,s), 3.73(3H,s), 3.77(3H,s), 3.93 ( 2H,t, J=6.0 Hz ), 4.10 ( 2H, t, J=6.0 Hz ), 6.25 (1H,s), 6.87(2H,d,J=8.8 Hz), 7.73(2H,m), 7.88 (2H,m), 7.91(2H,d,J=8.8 Hz).

Endo adduct of the title compound: yield: 59mg (35.7%). NMR(CDCl$_3$)δ(ppm): 2.23(2H,m), 3.46(3H,s), 3.56(3H,s), 3.63(3H,s), 3.80(2H,m), 3.92(2H,t,J=6.6 Hz), 4.10(2H,t,J=6.6 Hz), 5.98(1H,d,J=3.8 Hz), 6.81(2H,d,J=9.2 Hz), 7.74(2H,m), 7.83(2H,m), 7.98(2H,d,J=9.0 Hz).

EXAMPLE 2

7-[4-(3-Aminopropyloxy)phenyl]-8-hydroxypyrido[3,4-d]pyridazine-1,4(2H,3H)dione (L-011)

To a mixture of 0.57 g of exo form of cis-3,6-epoxy-4,5-dimethoxycarbonyl-3-methoxy-2-[4-(3-phthalimidopropyloxy)phenyl]-3,4,5,6-tetrahydropyridine and 0.5 g of end form thereof was added 1.5 ml of hydrazine monohydrate. The mixture was stirred under heating at 100° C. in a stream of nitrogen for 4 hours. The reaction mixture was neutralized with hyrochloric acid and adjusted to pH 5. The product was collected by filtration, dissolved in 1N sodium hydroxide and subjected to Amberlite ® XAD-2 [Rohm & Haas Co.] column chromatography (150×200). The fractions obtained by elution with 1N hydrochloric acid were combined. The solvent was distilled off. The resulting crystalline precipitate was collected by filtration with methanol. Yield: 76 mg. m.p. >300° C.

NMR(DMSO-d$_6$)δ(ppm): 2.08(2H,m), 2.98(2H,m), 4.16(2H,m), 7.08(2H,d,J=9.0 Hz), 8.05(3H,br.), 8.20(2H,d,J=9.0 Hz), 8.74(1H,s). IR(KBr)$\nu$: 3450, 2980, 2870, 1660, 1600, 1475, 1350, 1295, 1280 cm$^{-1}$. Elemental Analysis:Calcd. (C$_{16}$H$_{16}$N$_4$O$_4$.2HCl) C:47.89; H:4.52; N:13,96. Found C:47.59; H:4.60; N:13.96.

EXAMPLE 3

8-Amino-5-chloro-7-phenylpyrido[3,4-d]pyridazine-1,4(2H,3H)dione (L-012)

To 55 mg of 3-amino-6-chloro-4,5-diethoxycarbonyl-2-phenylpyridine as obtained in Reference Example 19 was added 1 ml of hydrazine monohydrate, and the mixture was heated at 100° C. in a stream of nitrogen for 25 minutes. Under ice-cooling, water was added to the reaction mixture. The mixture was neutralized with hydrochloric acid and adjusted to pH 5. The resulting yellow crystalline precipitate was collected by filtration.

Yield: 20 mg (43.9%). m.p. >300° C. NMR(DMSO-d$_6$)δ(ppm): 6.29(2H,s), 7.51-7.69(5H,m). IR(KBr)$\nu$: 3470, 3050, 1645, 1585 cm$^{-1}$. Elemental Analysis:- Calcd. (C$_{13}$H$_9$N$_4$O$_2$Cl) C:54.09; H:3.14; N:19.41. Found C:54.18; H:3.07; N:19.61.

REFERENCE EXAMPLE 26

3,4-Dimethoxycarbonyl-2-methoxy-5-nitro-6-phenylpyridine

In 25 ml of methanol was dissolved 1.2 g of 2-chloro-3,4-diethoxycarbonyl-5-nitro-6-phenylpyridine as obtained in Reference Example 18. To the solution was added 6.34 ml (2.0 eq.) of a solution of 1N sodium methoxide in methanol, and the mixture was stirred at room temperature for 30 minutes. The reaction mixture was neutralized with 0.2 ml (1.1 eq.) of acetic acid, and the solvent was distilled off. Water was added to the residue, and the mixture was extracted with ethyl acetate.

The organic layer was washed with water and a saturated aqueous solution of sodium chloride and dried. The solvent was distilled off. The residue was purified by silica gel column chromatography (eluent:ethyl acetate). The resulting crystals were collected by filtration with hexane.

Yield: 1.1 g (85.2%). NMR(CDCl$_3$)δ(ppm): 3.92(3H,s), 3.93(3H,s), 4.11(3H,s), 7.49(3H,m), 7.58(2H,m).

REFERENCE EXAMPLE 27

3-Amino-4,5-dimethyoxycarbonyl-6-methyoxy-2phenylpyridine

In 10 ml of ethyl acetate was dissolved 1.0 g of 3,4-dimethoyxcarbonyl-2-methoxy-5-nitro-6-phenylpyridine, and 500 mg of 10% Pd-C(50% wet) was added to the solution. Catalytic reduction reaction was conducted at room temperature for 3.5 hours. After the catalyst was removed by filtration, the filtrate was dried. The solvent was distilled off. The resulting crystals were collected by filtration with hexane.

Yield: 0.8 g (87.6%). NMR(CDCl$_3$)δ(ppm): 3.90(3H,s), 3.93(6H,s), 5.18(2H,br), 7.49(3H,m), 7.68(2H,m).

EXAMPLE 4

8-Amino-5-methoxy-7-phenylpyrido[3,4-d]pyridazine-1,4(2H,3H)dione (L-013)

To 0.8 g of 3-amino-4,5-dimethoxycarbonyl-6-methoxy-2-phenylpyridine was added 4 ml of hydrazine monohydrate. The mixture was heated at 100° C. in a stream of nitrogen for 1 hour. Under ice-cooling, water was added to the reaction mixture, followed by neutralization with hydrochloric acid for adjustment to pH 3. The resulting yellow crystalline precipitate was collected by filtration.

Yield: 0.7 g (98.7%) m.p. 250°–251° C. (dec.) NMR(DMSO-d$_6$)δ(ppm): 3.89(3H,s), 7.47(3H,m), 7.81(2H,dd,J=1.6, 8.4 Hz). IR(KBr)ν: 3450, 1645, 1530 cm$^{-1}$. Elemental Analysis:Calcd. (C$_{14}$H$_{12}$N$_4$O$_3$) C:59.15; H:4.25; N:19.71. Found C:59.11; H:4.13; N:19.49.

EXAMPLE 5

Comparison of Luminescent Intensity by Microperoxidase Catalyst

The pyridopyridazine compounds as obtained in Reference Examples 5 and 12, and Examples 1, 2, 3 and 4 and luminol (as obtained by recrystallization from a 5% aqueous solution of sodium hydroxide) were dissolved in 75 mM barbital buffer (pH 8.6) respectively at the concentrations of 100 ng/ml and 100 pg/ml. In test tubes were put 100 μl of the respective solutions. To each of the solutions was added 100 μl of 75 mM barbital buffer (pH 8.6) containing microperoxidase at 5 μg/ml and 100 μl of a 30 mM solution of H$_2$O$_2$ in distilled water, thereby to initiate chemiluminescent reaction. The chemiluminescent amounts were measured for 30 seconds with a measuring instrument equipped with the luminescent reader RLR-201 manufactured by Aloka. Taking the chemiluminescent amounts of luminol (sodium salt) at 10 ng/tube and 10 pg/tube respectively as 100, the relative luminescent intensities of the other pyridopyridazine compounds were calculated. The results are tabulated in Table 1. As shown in Table 1, the pyridopyridazine compounds exhibited as high as 55 times at maximum chemiluminescent intensities relative to that of luminol as taken as 100 as basis.

TABLE 1

| Relative luminescent intensity of various pyridopyridazine compounds | | | |
|---|---|---|---|
| (Abbreviated name) | | 10 pg/tube | 10 ng/tube |
| Reference Example | 5 (L-002) | 5541 | 1901 |
| | 12 (L-010) | 124 | 48 |
| Example | 1 (L-003) | 3740 | 1487 |
| | 2 (L-011) | 3533 | 1051 |
| | 3 (L-012) | 102 | 40 |
| | 4 (L-013) | 34 | 21 |
| Control Luminol (Na salt) | | 100 | 100 |

EXAMPLE 6

Comparison of Chemiluminescent Intensity by Peroxidase Catalyst 1

The pyridopyridazine compounds as obtained in Reference Example 12, Examples 3 and 4 and luminol were dissolved respectively at the concentration of 0.2 mM in 0.2 M Tris buffer (pH 8.6) containing 0.1 mM disodium ethylenediaminetetraacetate (EDTA). In test tubes were put 50 μl respectively of the solutions. To each of the solutions was added 100 μl of a solution of horseradish peroxidase dissolved at the concentration of 1 ng/ml and 10 ng/ml in 0.2 M Tris buffer (pH 8.6) and 50 μl of 0.2 M Tris buffer (pH 8.6) containing 0.6 mM H$_2$O$_2$, thereby to initiate chemiluminescent reaction.

The measurement was conducted for the luminous amounts for 10 seconds between 60 seconds later and 70 seconds later after addition of H$_2$O$_2$. The results are tabulated in Table 2. From Table 2, it is revealed that the pyridopyridazine compounds displayed 10 times at their maximum as high luminous amount as luminol (Na salt) did.

TABLE 2

| Luminous amount of pyridopyridazine compounds by peroxidase catalyst (without using enhancer). | | | | |
|---|---|---|---|---|
| Horseradish peroxidase ng/tube | Reference Example 12 (L-010) | Example 3 (L-012) | Example 4 (L-013) | Control (Luminol Na Salt) |
| 0.1 | 1.873 | 2.388 | 0.182 | 0.204 |
| 1 | 2.343 | 4.990 | 1.214 | 0.526 |

Unit: kilocount

EXAMPLE 7

Comparison of Chemiluminescent Intensity by Peroxidase Catalyst 2

The pyridopyridazine compound (L-012) as obtained in Example 3 and luminol were dissolved at the concentration of 0.2 mM in 0.2 M Tris buffer (pH 8.6) containing 0.1 mM EDTA. In test tubes were put 990 μl respectively of the solutions, and to each of the solutions was added 10 μl of a dimethylsulfoxide (DMSO) solution of 40 mM p-iodophenol as a chemiluminescent enhancer, followed by mixing. In other test tubes were put 50 μl of each of the mixtures, whereto 100 μl of a 0.2 M Tris buffer (pH 8.6) containing horseradish peroxidase at the concentrations of 10 pg/ml, 100 pg/ml 1 ng/ml or 10 ng/ml. By further adding 50 μl of Tris buffer (pH 8.6) containing of 0.6 mM H$_2$O$_2$ to each of the tubes, chemiluminescent reaction was initiated. The measurement was carried out for the luminous amounts for 10 seconds between 60 seconds later and 70 seconds later after addition of H$_2$O$_2$. The results are tabulated in Table 3. From Table 3, it was shown that the pyridopyridazine compound of Example 3 (L-012) provides about 4 to 20 times as great chemiluminescent amounts as luminol. The sodium salt of L-012 showed the same chemiluminescence activity as L-012.

TABLE 3

Luminous amount of pyridopyridazine compound by peroxidase catalyst (with an enhancer added)

| Horseradish peroxidase pg/tube | Example 3 (L-012) | Control (Luminol Na salt) |
|---|---|---|
| 1 | 0.678 | 0.032 |
| 10 | 3.128 | 0.295 |
| 100 | 115.638 | 28.288 |
| 1000 | 1184.635 | 294.160 |

Unit: kilocount

EXAMPLE 8

Relationship Between Amount of Antibody Labelled With Pyridopyridazine Compound and Luminous Count In 0.5 ml of dimethylformamide (DMF) was dissolved 5 μmol of the pyridopyridazine compound (L-011) as obtained in Example 2. To the solution, 0.1 ml of a DMF solution containing 7.5 μmol of succinic anhydride was added, and reaction was carried out at 4° C. overnight. To the reaction mixture, 0.1 ml of a DMF solution containing 5 μmol of N-hydroxysuccinimide and 0.1 ml of a DMF solution containing 8.5 μmol of dicyclohexylcarbodiimide were added, and the mixture was reacted further overnight, to obtain the active ester of L-011.

Prepared was a 0.05 M borate buffer (pH 8) solution containing monoclonal antibody against interferon γ (IFN-γ) at the concentration of 2.15 mg/ml. To 500 μl of the solution of antibody was added the aforesaid solution of the active ester in the proportion of L-011 to antibody of 20 to 1, and the mixture was reacted at 4° C. overnight. The resulting L-011-monoclonal anti-IFN-γ antibody-conjugate was purified by gel filtration with Sephadex ® G-25 Fine [Column capacity 10 ml, equilibrated with 0.05 M borate buffer (pH 8)].

Immunoassay with the prepared conjugate was conducted using polystyrene beads (Manufactured by Immunochemical, diameter: 3 mm) as the solid phase. The beads were immersed in a 50 μg/ml solution of IFN-γ in phosphate-buffered saline (PBS) and incubated at 4° C. overnight. After washing of the beads with PBS three times, the beads were immersed in PBS containing 25% Block-Ace ® (Manufactured by Snow Brand Milk Products) and preserved at 4° C. as they are until its use.

Prepared were conjugate solutions containing L-011-monoclonal anti-IFN-γ antibody-conjugate at concentrations of 10 μg/ml–10 pg/ml by diluting stepwise with PBS containing 25% Block-Ace ®. To 250 μl of each of the solutions was added a bead, followed by 2 hours' incubation at room temperature under shaking. After washing the beads with PBS five times, they were immersed in 250 μl of 2N sodium hydroxide solution and incubated at 100° C. for 1 hour to release L-011 from the antibody molecule. Using 100 μl of the supernatant containing L-011 in a free form, the amount of L-011 was determined by a chemiluminescence method. That is, chemiluminescence was initiated by adding 100 μl of 75 mM barbital buffer (pH 8.6) containing microperoxidase (MP-11) at 5 μg/ml and 100 μl of 75 mM barbital buffer containing 30 mM hydrogen peroxide, and measurement was conducted for 30 seconds with the luminescence reader RLR-201 (Manufactured by Aloka). The results are shown in FIG. 1. From the graph in FIG. 1 showing relationship between the amount of the anti-IFN-γ antibody labelled with the compound (L-011) and the luminous count, it is revealed that the luminous count increases as the amount of the antibody increases.

EXAMPLE 9

Sandwich Enzyme Immunoassay Method Using Chemiluminescent Detection Means (I).

Assay of human basic fibroblast growth factor (hbFGF) was conducted. The monoclonal antibody used (3H3) was obtained in accordance with Reference Example 28 as mentioned below.

1) Preparation of horseradish peroxidase-labelled antibody

The purified 3H3 antibody (7 mg/ml) was dialyzed against 0.1 M acetate buffer (pH 4.5) containing 0.1 M NaCl at 4° C. for 20 hours, followed by addition of pepsin (0.1 mg) (Sigma, U.S.A.). Then, digestion was carried out at 37° C. for 8 hours. The solution was adjusted to pH 8 with 1 M Tris to terminate the reaction. The resulting solution was placed on a column of Ultrogel AcA44 (IBF, France) and eluted with 0.02 M borate buffer (pH 8.0) containing 0.15 M NaCl to obtain F(ab')$_2$. The solution containing F(ab')$_2$ was concentrated to 1 ml. Then, the concentrated solution was dialyzed against 0.1 M phosphate buffer (pH 6.0) at 4° C. for 20 hours, and 0.1 ml of a solution [0.2 M mercaptoethylamine, 5 mM EDTA, 0.1 M phosphate buffer (pH 6.0)] was added, followed by reduction at 37° C. for 90 minutes. The reaction solution was placed on a Sephadex ® G-25 Fine column (1 cm diameter×60 cm, Pharmacia Fine Chemical, Sweden) and eluted with an eluent [5 mM EDTA, 0.1 M phosphate buffer (pH 6.0)] to obtain an Fab' fraction.

Additionally, 10 mg of horseradish peroxidase (HRP, Behringer Manheim, West Germany) was dissolved in 1.5 ml of 0.1 M phosphate buffer (pH 7.0), and 3.5 mg of N-(γ-maleimidobutyryloxy)succinimide (GMBS) was dissolved in 100 μl of N,N-dimethylformamide (DMF). The solution of GMBS in DMF was added to the HRP solution, followed by stirring at 30° C. for 60 minutes. Then, the resulting solution was placed on the Sephadex ® G-25 Fine column (1.2 cm diameter×60 cm) and eluted with 0.1 M phosphate buffer (pH 7.0) to obtain maleimido group introduced HRP (maleimidated HRP). Fab' and maleimidated HRP were mixed with each other to a mol ratio of 1:1, followed by reaction at 4° C. for 20 hours. The reaction solution was applied to an Ultrogel AcA44 column and eluted with 0.1 M phosphate buffer (pH 7.0) to obtain an enzyme labeled antibody (3H3-HRP).

2) preparation of antibody-combined solid phase

Monoclonal antibodies to hbFGF (MAb 52 and MAb 98) were diluted with 0.1 M carbonate buffer (pH 9.5) to the concentration of 50 μg/ml. In the resulting solution were immersed polystyrene beads of 3.2 mm in diameter, followed by standing at 4° C. overnight to sensitize. After washing the beads with 0.01 M phosphate buffer (pH 7.0) containing 0.15 M NaCl, the beads were immersed in 0.01 M phosphate buffer (pH 7.0) containing 0.1% BSA. Thus, the polystyrene beads were stored in a chilled place until its use.

3) Sandwich method-EIA (Chemiluminescent Method)

Into test tubes were put polystyrene beads as prepared in 2) mentioned above, and thereto were added 250 μl respectively of solutions of hbFGF dissolved at various concentrations in 0.02 M phosphate buffer (pH 7.0) containing 25% Block-Ace ® and 0.15 M NaCl (Buffer B), followed by reaction at 4° C. overnight. After washing each tube with PBS twice, 250 μl of horseradish peroxidase-labelled antibody solution (diluted 150 times with Buffer B) was added to each tube, followed by reaction at room temperature for 3 hours. After washing with PBS twice, 100 μl of 50 mM Tris buffer (pH 7.5) containing the pyridopyridazine compound (L-012) obtained in Example 3 at 200 μM, EDTA at 50 μM and 4-(4-hydroxyphenyl)thiazole as a chemiluminescent enhancer at 100 μM, and 100 μl of a 300 μM hydrogen peroxide solution were added to the reaction mixture, thereby to induce chemiluminescent reaction. Measurement was conducted by measuring chemiluminescent amounts for 10 seconds between 60 seconds later and 70 seconds later after addition of a hydrogen peroxide solution with the Aloka's luminescent reader.

Figure 2:
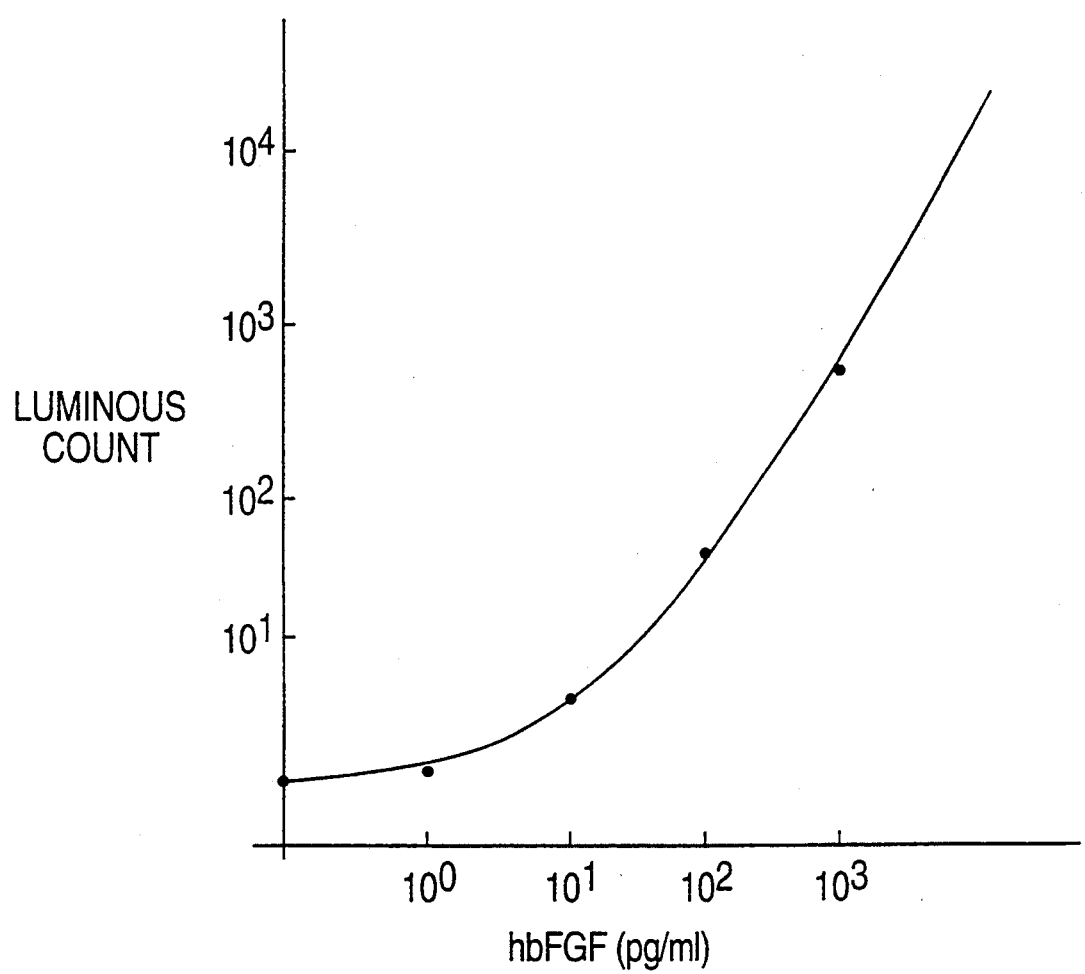
FIG. 2 shows the Calibration curve in the sandwich enzyme immunoassay of human basic fibroblast growth factor using chemiluminescence of the compound of Example 3 (L-012) for detection.

The obtained Calibration Curve of hbFGF is shown in FIG. 2. From the result, it was revealed that about 2 pg/ml of the hbFGF could be detected.

REFERENCE EXAMPLE 28

Preparation of monoclonal antibody 3H3
Immunization

BALB/c mice (female, 8 weeks old) were intraperitoneally injected with 50 μg of antigen rhbFGF mutein CS23 (a mutein in which each of Cys residues at positions 70 and 88 of human bFGF were substituted for a Ser residue) which was dissolved in Freund's complete adjuvant (Difco). Two weeks later, the mice were intraperitoneally given again 50 μg of antigen rhbFGF mutein CS23 dissolved in 0.4 ml of Freund's complete adjuvant. Further 2 weeks later, the mice were additionally immunized with 50 μg of antigen rhbFGF mutein CS23 dissolved in 0.4 ml of Freund's incomplete adjuvant. Two weeks after the additional immunization, 50 μg of rhbFGF mutein CS23 dissolved in PBS was inoculated into the tail veins of the mice.
Cell Fusion Three days after the final immunization, the spleens were removed from the mice immunized in Reference Example 28 to obtain cells to be used for cell fusion. These cells were suspended in medium of a mixture of Iscove's modified DMEM and Ham's F12 medium to the ratio of 1:1 (hereinafter referred to as IH medium).

Mouse myeloma cells SP2/0-AG14 (ATCC No. CRL 1581) were subcultured in DMEM medium containing 10% fetal calf serum under an atmosphere of 5% carbon dioxide and 95% air.

Cell fusion was carried out in accordance with the method established by Köhler and Milstein [G. Köhler and C. Milstein, Nature, 256, 495 (1975)]. The above myeloma cells ($2 \times 10^7$ cells) were mixed with the immunized lymphocytes ($1.5 \times 10^8$ cells) obtained by the above method, and the mixture was centrifuged. Then, 1 ml of a 45% solution of polyethylene glycol 6000 (hereinafter referred to as PEG 6000) in IH medium was dropwise added thereto. The PEG 6000 solution was preheated to 37° C. and slowly added for 1 minute.

Then, 1 ml of IH medium was added for 1 minute, 1 ml for 1 minute and 8 ml for 3 minutes. The solution was thereafter centrifuged at room temperature at 1,000 rpm for 5 minutes to remove a supernatant. The resulting cell precipitate was suspended in 30 ml of IH medium containing 20% calf serum. The suspension was seeded on a 96-well microtiter plate (Nunc) in an amount of 100 μl/well. One day later, IH medium (containing 20% calf serum) supplemented with HAT ($1 \times 10^{-4}$ M hypoxanthine, $4 \times 10^{-7}$ M aminopterin, $1.6 \times 10^{-5}$ M thymidine) was added to the microculture plate in an amount of 100 μl/well. The IH medium supplemented with HAT is hereinafter referred to as HAT medium. Further every 3 days, one-half the amount of the medium was exchanged for HAT medium. The cells which thus grew were hybrid cells.
Screening of Antibody-Producing Cells A fixing buffer [0.1 M sodium hydrogencarbonate (pH 9.6), 0.02% sodium azide] containing 200 ng/ml of rhbFGF mutein CS23 was added in an amount of 100 μl/well to a 96-well polystyrene microtiter plate (Nunc). After 2 hours, the microtiter plate was washed with a rinsing liquid (0.05% Tween 20, PBS), and then 100 μl of the combined solution of 50 μl of the culture supernatant and 50 μl of a buffer for dilution (0.05 M Tris-HCl buffer pH 8.01, 1 mM magnesium chloride, 0.15 M sodium chloride, 0.05% Tween-20, 0.02% sodium azide, 0.3% gelatin) was added to the microtiter plate. After 2 hours, the culture supernatant was washed with a rinsing liquid, followed by addition of the alkaline phosphatase-labelled goat anti-mouse IgG antibody (Bio RAD) as the second antibody. After 2 hours, the second antibody was washed with a rinsing liquid, and then color reaction was conducted by adding a reaction substrate (ELISA method). By this method, the rhbFGF mutein CS23 combining activity was observed in 4 wells.
Screening of Neutralizing
Antibody-Producing Cells Human umbilical vein-derived vascular endothelial cells was suspended in GIT medium (commercially available from Wako Pure Chemical Industries, Ltd. Japan; a mammalian serum-derived composition for animal cell cultivation, produced by subjecting mammalian serum to purifying treatment including an inactivation process for contaminant microorganisms and a salting-out/desalting process; cf. U.S. Pat. No. 4,654,304) containing 2.5% fetal calf serum, and the suspension was seeded in an amount of 100 μl/well (2,000 cells/well) to a 96-well microculture plate. The next day, GIT culture solution containing various concentrations of hybridoma culture supernatants, 4 ng/ml rhbFGF and 2.5% fetal calf serum was added in an amount of 100 μl/well, and cultivation was conducted at 37° C. under an atmosphere of 5% $CO_2$ and 7% $O_2$ for 3 days. After 3 days, the culture solution was removed, and then GIT medium containing 1 mg/ml MTT (4,5-dimethyl-2-thiazolyl-2,5-diphenyl-2H-tetrazolium bromide) and 2.5% fetal calf serum was added in an amount of 100 μl/well. After cultivation was carried out at 37° C. under an atmosphere of 5% $CO_2$ and 7% $O_2$ for 4 hours, 10% sodium dodecyl sulfate (SDS) was added in an amount of 100 μl/ml. After 4 hours, the absorbance at 590 nm was measured with a spectro-photometer for 96 wells (Titertek) (MTT method). By this method, the strong neutralizing activity was observed in one well.
Cloning of Hybrid Cells The cells in this well were seeded to 0.5 cell per well on a 96-well microculture plate on which mouse thymocytes had preliminarily been seeded as feeder cells, and cloning was carried out. As a result, hybridoma mouse 3H3 cells were obtained.

The cloned cells were suspended in IH medium containing 10%, dimethyl sulfoxide (DMSO), 10% calf serum, and stored in liquid nitrogen.

The culture supernatant of 3H3 cells obtained above were reacted with various immunoglobulin samples by a subclass detecting kit (Bio RAD). The results are shown in Table 4.

TABLE 4

| Immunoglobulin sample | 3H3 antibody |
| --- | --- |
| $IgG_1$ | + |
| $IgG_{2a}$ | − |
| $IgG_{2b}$ | − |
| $IgG_3$ | − |
| IgM | − |
| IgA | − |

In Table 4, "+" indicates that the reaction is positive, and "−" indicates that the reaction is negative.

Table 4 shows that the antibody in the culture supernatant of 3H3 cells belongs to $IgG_1$ in the immunoglobulin class.

Purification of Monoclonal Antibody from Culture Supernatant and Ascites

The combined solution of the culture supernatant of mouse 3H3 cells and a combining buffer [3 M sodium chloride, 1.5 M glycine (pH 8.7)] in a 1:1 ratio was loaded onto a protein A column. After washing with a combining buffer, elution was carried out with an elution buffer [0.1 M citric acid (pH 5)]. To the eluate was added 1 M Tris (pH 8.0) to neutralize it, followed by dialysis against PBS.

The IgG amount of the samples was determined according to the method described in the following manner. Various dilutions of mouse IgG whose concentration was known and the 3H3 antibody were fixed on a 96-well polystyrene microtiter plate with a fixing buffer. After 2 hours, the alkaline phosphatase-labelled goat anti-mouse IgG antibody (Bio RAD) was added thereto. After 2 hours, color reaction was conducted by adding a reaction substrate (ELISA method). With respect to mouse $IgG_1$, a determination curve was drawn, and the IgG amount of the samples was determined based on this curve, whereby a 60 μg/ml solution of the 3H3 antibody was prepared.

One μg/ml of the rabbit anti-bFGF polyclonal antibody was fixed and rhbFGF mutein CS23 was added thereto. Then, 1 μg/ml of the 3H3 antibody was added and 1 μg/ml of the alkaline phosphatase-labelled goat anti-mouse IgG antibody was further added thereto. By this method, rhbFGF mutein CS23 could be detected up to 3 ng/ml.

Further, the antibody was purified from ascites. The mouse 3H3 cell strain was injected into the mice (BALB/c). IgG was purified from the ascites according to conventional methods. Namely, 5 ml of the ascites was subjected to salt precipitation using a 45% saturated solution of ammonium sulfate, and the precipitate was dissolved in borate buffer (BBS, pH 8.5) containing 0.15 M NaCl, followed by dialysis against BBS at 4° C. for 20 hours. The dialyzed solution was applied to a DE-50 column (1 cm diameter×60 cm, Whatman, Great Britain), and the column was eluted with a linear gradient of 0.1 to 0.35 M NaCl in 0.1 M phosphate buffer (pH 8.0), whereby 7 mg of monoclonal antibody 3H3 was obtained from 5 ml of the ascites.

The hybridoma mouse 3H3 cells as obtained in the above-mentioned manner have been deposited in the Institute for Fermentation Osaka, Japan (IFO) under the accession number IFO 50216 since Nov. 10, 1989. The above cells have been also deposited with the Fermentation Research Institute, Agency of Industrial Science and Technology, Ministry of International Trade and Industry, Japan (FRI) under the accession number FERM BP-2658 since Nov. 14, 1989.

rhbFGF mutein CS23 was produced using transformant Escherichia coli MM294/pTB762 (IFO 14613, FERM BP-1645) by the methods described in Seno et al., Biophys. Biochem. Res. Commun. 151, 701 (1988) and European Patent Publication No. 281,822 was used. The above E. coli MM294/pTB762 was deposited with IFO under the accession number IFO 14613 on May 27, 1987. This transformant was also deposited with FRI under the accession number FERM P-9409 on Jun. 11, 1987. This 10 deposit was converted to the deposit under the Budapest Treaty and the transformant is stored at the FRI under the accession number FERM BP-1645.

REFERENCE EXAMPLE 29

3-Amino-4,5-diethoxycarbonyl-6-hydroxy-2-phenylpyridine

After a mixture of 500 mg of 3,4-diethoxycarbonyl-5-nitro-6-phenyl-2-pyridone as obtained in Reference Example 17, 690 mg of reduced iron and 5 ml of ethanol was heated to 60° C., 2.83 ml of conc. hydrochloric acid was added dropwise over 30 minutes. The mixture was neutralized with a saturated aqueous solution of sodium hydrogencarbonate, followed by extraction with dichloromethane. After the organic layer was dried, the solvent was distilled off. The residue was purified by silica gel column (eluent: ethyl acetate/dichloromethane 1:6), to afford crude crystals. Recrystallization of the crude crystals from dichloromethane-hexane gave orange crystalline precipitate.

Yield: 102 mg(22.3%). m.p. 103°–104° C. NMR(CDCl$_3$) δ (ppm): 1.40(6H,m), 4.05(2H,s), 4.41(4H,m), 7.47(3H,m), 7.67(2H,m). IR(KBr)ν: 1740, 1720, 1635, 1580 cm$^{-1}$.

REFERENCE EXAMPLE 30

3,4-Diethoxycarbonyl-2-dimethylamino-5-nitro-6-phenylpyridine

In 1 ml of ethanol was dissolved 100 mg of 2-chloro-3,4-diethoxycarbonyl-5-nitro-6-phenylpyridine as obtained in Reference Example 18, whereto 0.34 ml (2.0 eq.) of a 1.55 M ethanol solution of dimethylamine was added. The mixture was stirred at room temperature for 1.5 hours. Thereafter, 0.1 ml of the same solution of dimethylamine was added. The mixture was left standing overnight. After the solvent was distilled off, the resulting crystals were collected by filtration with hexane.

Yield: 51.7 mg (50.5%). NMR(CDCl$_3$) δ (ppm): 1.37(6H,t,J=7.2 Hz), 3.17(6H,s), 4.35(2H,q,J=7.2 Hz), 4.40(2H,q,J=7.2 Hz), 7.45(3H,m), 7.60(2H,m).

REFERENCE EXAMPLE 31

3-Amino-4,5-diethoxycarbonyl-6-dimethylamino-2-phenylpyridine

In 2 ml of ethyl acetate Was dissolved 52 mg of 3,4-diethoxycarbonyl-2-dimethylamino-5-nitro-6-phenylpyridine, whereto 50 mg of 10% Pd-C (50% wet) was added. Catalytic reduction reaction was conducted for 5.5 hours. After the catalyst was removed, the solvent was distilled off and the residue was purified by silica gel column chromatography (eluent: ethyl acetate/hexane 1:2).

Yield: 43 mg (89.6%). NMR(CDCl$_3$) δ(ppm): 1.37(3H,t,J=7.2 Hz), 1.39 (3H,7,J=7.2 Hz), 2.80(6H,s), 4.36(4H,m), 5.08(2H,br.), 7.47(3H,m), 7.66(2H,m).

REFERENCE EXAMPLE 32

3,4-Diethoxycarbonyl-6-methyl-2-pyridone

In 90 ml of 2% hydrochloric acid was dissolved 2.52 g (10 mmol) of 2-amino-3,4-diethoxycarbonyl-6-methylpyridine. A solution of 0.83 g (1.2 eq.) of sodium nitrite dissolved in 3 ml of water was added dropwise to the solution. The mixture was stirred at room temperature for 1 hour and left standing in a refrigerator overnight. The resulting crystals were collected by filtration. The crystals were recrystallized from ethyl acetate to give colorless plates.

Yield: 1.5 g (59.3%). m.p. 138°–139° C. NMR(CDCl$_3$) δ(ppm): 1.36(6H,t,J=7.2 Hz), 2.37(3H, s), 4.32(2H,q,J=7.2 Hz), 4.36(2H,q,J=7.2 Hz), 6.43(1H,s). IR(KBr)ν: 1755, 1725, 1635, 1260 cm$^{-1}$. Elemental Analysis:Calcd. (C$_{12}$H$_{15}$NO$_5$)C: 56.91, H:5.97; N:5.53. Found C:56.96; H:6.04; N:5.39.

REFERENCE EXAMPLE 33

3,4-Diethoxycarbonyl-6-methyl-5-nitro-2-pyridone

In 13 ml of acetic anhydride was suspended 5.0 g of 3,4-diethyoxycarbonyl-6-methyl-2-pyridone, and the suspension was cooled to −10° C., whereto 1.22 ml (2.1 eq.) of fuming nitric acid was added dropwise over 30 minutes. The mixture was stirred for 30 minutes. After 40 ml of water was added, the mixture was stirred overnight at room temperature. The resulting crystals were collected by filtration and dried.

Yield: 2.19 g (37.2%). The crystals were recrystallized from dichloromethane-isopropyl ether to give pale yellow prisms. m.p. 134°–135° C. NMR(CDCl$_3$) δ(ppm): 1.36(6H,t,J=7.2 Hz), 2.72(3H,s), 4.38(4H,q,J=7.2 Hz). IR(KBr) ν: 3420, 1755, 1650, 1525, 1350, 1270 cm$^{-1}$. Elemental Analysis: Calcd. (C$_{12}$H$_{14}$N$_2$O$_7$) C: 48.33, H:4.73; N:9.39. Found C:48.41; H:4.76; N:9.36.

REFERENCE EXAMPLE 34

2-Chloro-3,4-diethoxycarbonyl-6-methyl-5-nitropyridine.

To 1.0 g of 3,4-diethoxycarbonyl-6-methyl-5-nitro-2-pyridone was added 1.3 ml (3.2 eq.) of phenylphosphonic dichloride. The mixture was heated at 170° C. for 20 mintues. Water was added to the reaction mixture, followed by extraction with ethyl acetate. The organic layer was washed with water and a saturated aqueous solution of sodium chloride and dried over magnesium sulfate. After the solvent was distilled off, the residue was purified by silica gel column chromatography (eluent:ethyl acetate) to give an oily product.

Yield: 360 mg (34.0%). NMR(CDCl$_3$) δ (ppm): 1.34(3H,t,J=7.1 Hz), 1.40(3H,t,J=7.1 Hz), 2.68(3H,s), 4.41(4H,m). IR(KBr) ν: 2990, 1750, 1590, 1550 cm$^{-1}$.

REFERENCE EXAMPLE 35

3-Amino-6-choro-4,5-diethyoxycarbonyl-2-methylpyridine

In 15 ml of ethanol was dissolved 1.2 g of 2-chloro-3,4-diethoxycarbonyl-6-methyl-5-nitropyridine, whereto 1.9 g (9 eq.) of reduced iron was added, followed by adding dropwise 7.1 ml of hydrochloric acid. The mixture was stirred at room temperature for 30 minutes. After the solvent was distilled off, the residue was neutralized with sodium hydrogencarbonate, followed by extraction with ethyl acetate. The organic layer was washed with a saturated aqueous solution of sodium chloride and dried. The solvent was distilled off to give an oily product.

Yield: 1.1 g. NMR(CDCl$_3$) δ (ppm): 1.36(3H,t,J=7.0 Hz), 1.40(3H,t,J=7.2 Hz), 2.45(3H,s), 4.35(2H,q,J=7.2 Hz), 4.40(2H,q,J=7.0 Hz). 5.72(2H,br.). IR(neat) ν: 3500, 3000, 1740, 1710, 1255 cm$^{-1}$.

EXAMPLE 10

8-Amino-7-methylpyrido[3,4-d]pyridazine-1,4(2H,3H)dione (L-023)

To 57 mg of 3-amino-6-chloro-4,5-diethoxycarbonyl-2-methylpyridine was added 0.5 ml of hydrazine monohydrate, and the mixture was heated in a stream of nitrogen at 100° C. for 30 minutes. The solvent is distilled off, and the resultant crystals were collected by filtration with ethanol. After water was added to the crystals, the mixture was neutralized with 1N hydrochloric acid.

Yield: 37 mg (85.2%). m.p. >300° C. NMR(DMSO-d$_6$) δ(ppm): 2.43(3H,s), 7.16(2H,br.), 8.18(1H,s). IR(KBr) ν: 3430, 3350, 3240, 1655, 1590 cm$^{-1}$. Elemental Analysis: Calcd. (C$_8$H$_8$N$_4$O$_2$.0.1H$_2$O) C: 49.54, H:4.26; N:28.88. Found C:49.66; H:4.11; N:29.04.

REFERENCE EXAMPLE 36

4-Methoxyacetophenone

In 200 ml of ethanol was dissolved 30.0 g of 4-hydroxyacetophenone, and a solution of 11.3 g (1.28 eq.) of sodium hydroxide in 60 ml of water and 33.9 g (1.22 eq.) of dimethyl sulfate were added dropwise consecutively. After the reaction mixture was refluxed for 30 minutes', a solution of 2.8 g (0.32 eq.) of sodium hydroxide dissolved in 10 ml of water was added, followed by heating under for 3 hours' reflux. After the solvent was distilled off, water was added and the mixture was extracted with ethyl acetate. The organic layer was washed with water and a saturated aqueous solution of sodium chloride, and dried. Then, the solvent was distilled off. The resulting crystals were collected by filtration with hexane.

Yield: 26.1 g (78.8%). NMR(CDCl$_3$) δ (ppm): 2.57(3H,s), 3.88(3H,s), 6.94(2H,d,J=9.0 Hz), 7.95(2H,d,J=9.0 Hz).

REFERENCE EXAMPLE 37

Ethyl 3-(4-methoxybenzoyl)pyruvate

In 100 ml of ethanol was dissolved 4.2 g (1.1 eq.) of sodium, and a mixture of 25.0 g of 4-methoxyacetophenone and 27 ml (1.2 eq.) of diethyl oxalate was added dropwise under reflux. After 2 hours' reflux, the resulting crystals were collected by filtration. After 200 ml of 1N hydrochloric acid was added, the mixture was extracted with ethyl acetate. The organic layer was washed with water and a saturated aqueous solution of sodium chloride and dried. The solvent was distilled off. The resulting crystals were collected by filtration with hexane.

Yield: 34.7 g (83.1%). NMR(CDCl$_3$) δ (ppm): 1.42(3H,t,J=7.1 Hz), 3.90(3H,s), 4.40(2H,q,J=7.2 Hz), 6.99(2H,d,J=9.0 Hz), 7.04(1H,s), 8.00(2H,d,J=9.0 Hz).

REFERENCE EXAMPLE 38

2-Amino-3,4-diethoxycarbonyl-6-(4-methoxyphenyl)-pyridine

A mixture of 4.0 g of ethyl 3-(4-methoxybenzoyl)-pyruvate and 5.34 g (2.1 eq.) of ethyl 3-amino-3-ethoxyacrylate was heated at 100° C. under reduced pressure for 1 hour while low boiling substances were distilled off. The crystals resulting from addition of 25 ml of 10% hydrochloric acid were collected by filtration with ethanol. After an aqueous solution of sodium hydrogencarbonate was added, the mixture was extracted with ethyl acetate. The organic layer was washed with water and a saturated aqueous solution, and dried. The solvent was distilled off. The resulting crystals were collected by filtration with hexane.

Yield: 2.7 g (48.7%). NMR(CDCl$_3$) δ (ppm): 1.35(3H,t,J=7.1 Hz), 1.39(3H, t,J=7.2 Hz), 3.87(3H,s), 4.33(2H, q,J=7.0 Hz), 4.38(2H,q,J=7.2 Hz), 6.42(2H, br.), 6.97(2H,d,J=8.8 Hz), 7.02(1H,s), 7.97(2H, d,J=9.0 Hz). IR(KBr) ν: 3470, 3350, 1725, 1695, 1600, 1565 cm$^{-1}$.

REFERENCE EXAMPLE 39

3,4-Diethoxycarbonyl-6-(4-methoxyphenyl)-2-pyridone

To 100 mg of 2-amino-3,4-diethoxycarbonyl-6-(4-methoxyphenyl)pyridine were added 2 ml of 1N hydrochloric acid and 5 ml of dioxane, and thereto was added dropwise a solution of 26 mg (1.3 eq.) of sodium nitrite dissolved in 0.5 ml of water under ice-cooling. The mixture was stirred at room temperature overnight. The solvent was distilled off. The residue was neutralized with sodium hydrogencarbonate, followed by extraction with ethyl acetate. The organic layer was washed with a saturated aqueous solution of sodium chloride and dried. The solvent was distilled off. The resulting crude crystals were recrystallized from ethanol.

Yield: 47 mg (46.8%). NMR(CDCl$_3$) δ (ppm): 1.37(3H,t,J=7.2 Hz), 1.39(3H,t,J=7.1 Hz), 3.88(3H,s), 4.39(2H,q,J=7.2 Hz), 4.41(2H,q,J=7.2 Hz), 6.96(1H,s), 7.01(2H,d,J=9.0 Hz), 7.81(2H,d,J=8.8 Hz). IR(KBr) ν: 1740, 1725, 1630, 1600, 1520, 1265, 1165 cm$^{-1}$.

REFERENCE EXAMPLE 40

3,4-Diethoxycarbonyl-6-(4-methoxyphenyl)-5-nitro-2(1H)pyridone

In 8 ml of acetic anhydride was suspended 1.2 g of 3,4-diethoxycarbonyl-6-(4-methoxyphenyl)-2(1H)pyridone. After the mixture was cooled to −30° C. 0 36 ml of fuming nitric acid was added dropwise, followed by stirring for 45 minutes. After water was added, stirring was continued for further 1 hour. The viscous product was collected by filtration, crystallized with diethyl ether and washed.

Yield: 0.62 g (45.4%). NMR(CDCl$_3$) δ (ppm): 1.37(6H,t,J=7.2 Hz), 3.87(3H,s), 4.40(2H,q,J=7.2 Hz), 4.42(2H,q,J=7.2 Hz), 6.99(2H,d,J=8.8 Hz), 7.52(2H,d,J=8.8 Hz). IR(KBr) ν: 1740, 1655, 1610, 1260 cm$^{-1}$.

REFERENCE EXAMPLE 41

2-Chloro-3,4-diethoxycarbonyl-6-(4-methoxyphenyl)-5-nitropyridine

To 300 mg of 3,4-diethoxycarbonyl-6-(4-methoxyphenyl)-5-nitro-2(1H)pyridone were added 0.5 ml of phosphorus oxychloride and two drops of DMF. The mixture was heated at 100° C. for 1 hour. After ice water was added, the mixture was neutralized with sodium hydrogencarbonate, followed by extraction with ethyl acetate. The organic layer was washed with water and a saturated aqueous solution of sodium chloride and dried. The solvent was distilled off. The residue was purified by silica gel column chromatography (eluent:ethyl acetate/hexane 1:1).

Yield: 270 mg (86.0%). NMR(CDCl$_3$) δ (ppm): 1.35(3H,t,J=7.0 Hz), 1.41(3H,t,J=7.2 Hz), 3.87(3H,s), 4.39(2H,q,J=7.0 Hz), 4.46(2H,q,J=7.2 Hz), 6.98(2H,d,J=8.8 Hz), 7.59(2H,d,J=8.8 Hz). IR(neat) ν: 2970, 1750, 1610, 1575, 1540, 1260 cm$^{-1}$.

REFERENCE EXAMPLE 42

3-Amino-6-chloro-4,5-diethoxycarbonyl-2-(4-methoxyphenyl)pyridine

In 4 ml of ethanol was dissolved 280 mg of 2-chloro-3,4-diethyoxycarbonyl-6-(4-methoxyphenyl)-5-nitropyridine, whereto 340 mg(8.9 eq.) of reduced iron was added. After the mixture was heated to 60° C., 1.5 ml of conc. hydrochloric acid was added dropwise and the mixture was refluxed. After heating for 20 minutes, the solvent was distilled off. The residue was neutralized with an aqueous solution of sodium hydrogencarbonate, followed by extraction with ethyl acetate. After the precipitate was filtered off, the obtained organic layer was washed with water and a saturated aqueous solution of sodium chloride, and dried. Thereafter, the solvent was distilled off.

Yield: 213 mg (82.4%).

NMR(CDCl$_3$) δ (ppm): 1.37(3H,t,J=7.1 Hz), 1.43(3H,t,J=7.2 Hz), 3.86(3H,s), 4.36(2H,q,J=7.1 Hz), 4.42(2H,q,J=7.2 Hz), 5.93(2H,br.), 7.01(2H,d,J=8.8 Hz), 7.56(2H,d,J=8.8 Hz). IR(neat) ν: 3480, 3360, 2980, 1735, 1700, 1605, 1515 cm$^{-1}$.

EXAMPLE 11

8-Amino-5-chloro-7-(4-methoxyphenyl)pyrido[3,4-d]pyridazine-1,4-(2H,3H)dione (L-024)

To 210 mg of 3-amino-6-chloro-4,5-diethoxycarbonyl-2-(4-methoxyphenyl)pyridine was added 3 ml of hydrazine monohydrate, and the mixture was heated at 100° C. in a stream of nitrogen for 30 minutes. After solvent was distilled off, the resulting crystals were collected by filtration with ethanol. Water was added to the crystals, and the mixture was neutralized with 1N hydrochloric acid, followed by collection of the crystals by filtration.

Yield: 104 mg (58%). m.p. >300° C. NMR(DMSO-d$_6$) δ (ppm): 3.83(3H,s), 7.08(2H,d,J=8.8 Hz), 7.36(2H,br.), 7.64(2H,d,J=8.8 Hz). IR(KBr) ν: 1645, 1605, 1495, 1250 cm$^{-1}$. Elemental Analysis: Calcd. ($C_{14}H_{11}N_4O_3Cl.0.1H_2O$) C:52.46; H:3.52; N:17.48. Found C:52.23; H:3.54; N:17.68.

REFERENCE EXAMPLE 43

3-Amino-4,5-diethoxycarbonyl-2-methylpyridine

Catalytic reduction was carried out using 1.5 g of 3-amino-6-chloro-4,5-diethoxycarbonyl-2-methylpyridine as obtained in Reference Example 35, 1 ml (2 eq.) of triethylamine, 50 ml of ethyl acetate and 1.5 g of 10% Pd-C(50% wet). The catalyst was removed by filtration and the solvent was distilled off. The residue was purified by silica gel column chromatography (eluent:ethyl acetate/dichloromethane 1:1) to give 1.1 g of the title compound as an oily product.

NMR(CDCl$_3$) δ (ppm): 1.35(3H,t,J=7.1 Hz), 1.37(3H,t,J=7.1 Hz), 2.45(3H,s), 4.34(2H,q,J=7.1 Hz), 4.36(2H,q,J=7.1 Hz), 4.98(2H,br.), 8.16(1H,s). IR(neat) ν: 1720, 1615, 1415, 1305, 1275, 1240 cm$^{-1}$.

EXAMPLE 12

8-Amino-7-methylpyrido[3,4-d]pyridazine-1,4(2H,3H)dione (L-026)

To 57 mg of 3-amino-4,5-diethoxycarbonyl-2-methylpyridine was added 0.5 mL of hydrazine monohydrate, and the mixture was heated at 100° C. in a stream of nitrogen for 30 minutes. After the solvent was distilled off, the resulting crystals were collected by filtration with ethanol. Water was added to the crystals, and the mixture was neutralized with 1N hydrochloric acid, followed by collection of the crystals by filtration.

Yield: 37 mg (85.2%). m.p. >300° C. NMR(DMSO-d$_6$) δ (ppm): 2.43(3H,s), 7.16(2H,br.), 8.18(1H,s). IR(KBr) ν: 3430, 3350, 3240, 1655, 1590 cm$^{-1}$. Elemental Analysis: Calcd. (C$_8$H$_8$N$_4$O$_2$.0.1H$_2$O) C:49.54; H:4.26; N:28.88. Found: C:49.66; H:4.11; N:29.04.

REFERENCE EXAMPLE 44

4-Methoxyethoxymethoxyacetophenone.

In 160 ml of dichloromethane was dissolved 16 g of 4-hydroxyacetophenone, whereto 307 ml (1.5 eq.) of diisopropylethylamine was added and 20.13 ml (1.5 eq.) of methoxyethoxymethyl chloride was added dropwise. The mixture was stirred at room temperature for 4 hours and washed with water. After the organic layer was dried, the solvent was distilled off. The residue was purified by silica gel column chromatography (eluent: :ethyl acetate-hexane 1:2)

Yield: 29.5 g. NMR(CDCl$_3$) δ (ppm): 2.56(3H,s), 3.37(3H,s), 3.55(2H,m), 3.83(2H,m), 5.34(2H,s), 7.10(2H,d,J=9.0 Hz), 7.94(2H,d,J=8.8 Hz).

REFERENCE EXAMPLE 45

Ethyl 3-(4-methoxyethoxymethoxy)benzoylpyruvate

In 75 ml of ethanol was dissolved 3.2 g (1.1 eq.) of sodium, whereto a mixture of 28.5 g of 4-methoxyethoxymethoxyacetophenone and 20.7 ml (1.2 eq.) of ethyl oxalate was added dropwise over 30 minutes. The mixture was stirred for 1.5 hours. After the solvent was distilled off, water was added to the residue and the mixture was neutralized with 1N hydrochloric acid, followed by extraction with ethyl acetate.

The organic layer was washed with water and a saturated aqueous solution of sodium chloride, and dried. Then, the solvent was distilled off.

Yield: 38.7 g(94%). NMR(CDCl$_3$) δ (ppm): 1.42(3H,t,J=7.1 Hz), 3.37(3H,s), 3.55(2H,m), 3.83(2H,m), 4.40(2H,q,J=7.2 Hz), 5.36(2H,s), 7.03(1H,s), 7.15(2H,d,J=9.0 Hz), 7.98(2H,d,J=9.0 Hz).

REFERENCE EXAMPLE 46

2-Amino-3,4-diethoxycarbonyl-6-(4-methoxyethoxymethoxyphenyl)pyridine.

A mixture of 38.7 g of ethyl 3-(4methoxyethoxymethoxy)benzoylpyruvate and 39.9 g (2.1 eq.) of ethyl 3-amino-3-ethoxyacrylate was heated at 100° C. while stirring. While the low boiling substances were distilled off under reduced pressure, heating was conducted for 3 hours. Water was added to the reaction mixture, followed by extraction with ethyl acetate. The organic layer was washed with water and a saturated aqueous solution of sodium chloride and dried. After the solvent was distilled off, the residue was purified by silica gel column chromatography (eluent:ethyl acetate/hexane 1:3)

Yield: 32.2 g(64.5%). NMR(CDCl$_3$) δ (ppm): 1.35(3H,t,J=7.1 Hz), 1.39(3H,t,J=7.1 Hz), 3.38(3H,s), 3.56(2H,m), 3.84(2H,m), 4.33(2H,q,J=7.2 Hz), 4.38(2H,q,J=7.2 Hz), 5.33(2H,s), 6.41(2H,br.), 7.02(1H,s), 7.12(2H,d,J=9.0 Hz), 7.95(2H,d,J=9.0 Hz).

REFERENCE EXAMPLE 47

3,4-Diethoxycarbonyl-6-(4-methoxyethoxymethoxyphenyl)-2-pyridone.

In 250 ml of 1N hydrochloric acid and 100 ml of dioxane was dissolved 32.2 g of 2-amino-3,4-diethoxycarbonyl-6-(4-methoxyethoxymethoxyphenyl)pyridine, whereto a solution of 6.9 g (1.3 eq.) of sodium nitrite dissolved in 30 ml of water was added dropwise under ice-cooling. The mixture was stirred for 1 hour and left standing in a refrigerator overnight. The mixture was neutralized with sodium hydrogencarbonate, and dioxane was distilled off, followed by extraction with ethyl acetate. The organic layer was washed with a saturated aqueous solution of sodium chloride and dried. Then, the solvent was distilled off. The residue was purified by silica gel column chromatography (eluent:dichloromethane→ethyl acetate).

Yield: 18.1 g(56%). NMR(CDCl$_3$) δ (ppm): 1.38(3H,t,J=7.1 Hz), 1.39(3H,t,J=7.2 Hz), 3.39(3H,s), 3.58(2H,m), 3.84(2H,m), 4.39(2H,q,J=7.1 Hz), 4.41(2H,q,J=7.2 Hz), 5.33(2H,s), 6.96(1H,s), 7.30(2H,d,J=9.0 Hz), 7.80(2H,d,J=9.0 Hz). IR(KBr) ν: 2980, 2930, 1730, 1640, 1605, 1520, 1255, 1190 cm$^{-1}$.

REFERENCE EXAMPLE 48

3,4-Diethoxycarbonyl-2-hydroxy-6-(4-methoxyethoxymethoxyphenyl)-5-nitropyridine

In 3 ml of acetic anhydride was dissolved 1.0 g of 3,4-diethoxycarbonyl-6-(4-methoxyethoxymethoxyphenyl)-2-pyridone, and the mixture was cooled to −20° C. and thereafter 0.2 ml of fuming nitric acid was added dropwise. After the mixture was stirred for 1 hour, water was added. After 2 hours' stirring at room temperature, the mixture was extracted with ethyl acetate. The organic layer was washed with an aqueous solution of sodium hydrogencarbonate, water and a saturated aqueous solution of sodium chloride, and dried. After the solvent was distilled off the resulting crystals were collected by filtration with diethyl ether.

Yield: 198 mg(17.9%). NMR(DMSO-d$_6$) δ (ppm): 1.22(6H,t,J=7.1 Hz), 3.22(3H,s), 3.45(2H,m), 3.71(2H,m), 4.28(4H,m), 5.26(2H,s), 7.04(2H,d,J=8.8 Hz.), 7.25(2H,d,J=8.8 Hz). IR(KBr) ν: 1770, 1720, 1570, 1230 cm$^{-1}$.

REFERENCE EXAMPLE 49

2-Hydroxy-6-(4-hydroxyphenyl)-3,4-diethoxy-carbonyl-5-nitropyridine.

In 30 ml of dichloromethane was dissolved 2.2 g of 3,4-diethoxycarbonyl-2-hydroxy-6-(4-methoxyethoxymethoxyphenyl)-5-nitropyridine (crude product), whereto 2.6 ml of titanium tetrachloride was added dropwise under ice cooling. After the mixture was stirred for 1.5 hours at room temperature, water was added. The solvent was distilled off, followed by extraction with ethyl acetate. The organic layer was washed with water and a saturated aqueous solution of sodium chloride, and dried. Then, the solvent is distilled off, followed by crystallization from diethyl ether and collection of the resulting crystals by filtration.

Yield: 330 mg. NMR(CDCl$_3$) δ (ppm): 1.38(6H,t,J=7.1 Hz), 4.41(4H,m) 6.90(2H,d,J=8.82 Hz), 7.45(2H,d,J=8.8 Hz). IR(KBr) ν: 1730, 1650, 1605, 1280 cm$^{-1}$.

REFERENCE EXAMPLE 50

2-Chloro-3,4-diethoxycarbonyl-6-(4-hydroxyphenyl)-5-nitropyridine

In 2.5 ml of phosphorus oxychloride was suspended 130 mg of 3,4-diethoxycarbonyl-2-hydroxy-6-(4-hydroxyphenyl)-5-nitropyridine, whereto 0.4 ml of DMF was added. The mixture was heated at 100° C. for 30 minutes. Then, 0.4 ml of DMF was added and the mixture was heated for further 30 minutes. After the solvent was distilled off, ice-water was added, followed by neutralization with sodium hydrogencarbonate and extraction with ethyl acetate. After the organic layer was washed with water and a saturated aqueous solution of sodium chloride and dried, the solvent was distilled off. The residue was purified by silica gel column chromatography (eluent:ethyl acetate).

Yield: 117 mg(85%, in a mixture with about 20% of O-formyl compound). NMR(CDCl$_3$) δ (ppm): 1.34(3H,t,J=7.2 Hz), 1.41(3H,t,J=7.2 Hz), 4.38(2H,q,J=7.2 Hz), 4.45(2H,q,J=7.2 Hz), 6.92(2H,d,J=8.6 Hz), 7.52(2H,d,J=8.6 Hz).

REFERENCE EXAMPLE 51

3-Amino-6-chloro-3,4-diethoxycarbonyl-6-(4-hydroxyphenyl)pyridine

In 50 ml of ethanol was dissolved 800 mg of 2-chloro-3,4-diethoxycarbonyl-6-(4-hydroxyphenyl)-5-nitropyridine, whereto 1.0 g (8.8 eq.) of reduced iron was added. After the mixture was heated to 60° C., 4 me of conc. hydrochloric acid was added dropwise, and the mixture was refluxed for 1.5 hours. Then, 250 mg of reduced iron and 0.4 ml of conc. hydrochloric acid were added, followed by 3 hours' reflux. After the solvent was distilled off, the residue was neutralized with sodium hydrogencarbonate, followed by extraction with ethyl acetate. After the precipitate was removed by filtration, the obtained organic layer was washed with water and a saturated aqueous solution and dried. Then, the solvent was distilled off.

Yield: 530 mg(71.7%). NMR(CDCl$_3$) δ (ppm): 1.37(3H,t,J=7.2 Hz), 1.43(3H,t,J=7.2 Hz), 4.37(2H,q,J=7.2 Hz), 4.43(2H,q,J=7.2 Hz), 5.92(2H,br.), 6.92(2H,d,J=8.4 Hz), 7.48(2H,d,J=8.4 Hz). IR(neat) ν: 1735, 1700, 1605, 1590 cm$^{-1}$.

EXAMPLE 13

8-Amino-5-chloro-7-(4-hydroxyphenyl)pyrido[3,4-d]-pyridazine-1,4(2H,3H)dione (L-027)

To 200 mg of 3-amino-6-chloro-3,4-diethoxycarbonyl-2-(4-hydroxyphenyl)pyridine was added 2 ml of hydrazine monohydrate, and the mixture was heated at 100° C. in a stream of nitrogen for 1 hour. After the solvent was distilled off, the resulting crystals were collected by filtration with ethanol. Water was added to the crystals, and the mixture was neutralized with 1N hydrochloric acid. The resulting crystals were collected by filtration and then dissolved in methanol, followed by purification by octadecylsilylated silica gel (ODS) column chromatography. The crystals were collected by filtration with water.

Yield: 128 mg(86.7%). m.p. >300°. NMR(DMSO-$_6$) δ (ppm): 6.90(2H,d,J=8.6 Hz), 7.53(2H,d,J=8.6 Hz), 9.84(1H,s). IR(KBr) ν: 1650, 1610 cm$^{-1}$. Elemental Analysis: Calcd. (C$_{13}$H$_9$N$_4$O$_3$Cl.0.9H$_2$O) C:48.66; H:3.39; N:17.46. Found C:48.89; H:3.55; N:17.23.

REFERENCE EXAMPLE 52

2-Bromo-3,4-diethoxycarbonyl-5-nitro-6-phenylpyridine

To 0.5 g of 3,4-diethoxycarbonyl-5-nitro-6-phenyl-2(1H)pyridone as obtained in Reference Example 17 was added 7 g of phosphoryl bromide, and the mixture was heated to 100° C. After adding 0.5 ml of DMF dropwise, the mixture was heated for 15 minutes. After ice-water was added, the mixture was neutralized with sodium hydrogencarbonate, followed by extraction with ethyl acetate. The organic layer was washed with water and a saturated aqueous solution of sodium chloride, and dried, followed by removal of the solvent by distillation.

Yield: 0.54 g(92%). NMR(CDCl$_3$) δ (ppm): 1.34(3H,t,J=7.2 Hz), 1.43(3H,t,J=7.2 Hz), 4.39(2H,q,J=7.2 Hz), 4.47(2H,q,J=7.2 Hz), 7.52(5H,m). IR(neat) ν: 1740, 1570, 1540, 1255, 1220 cm$^{-1}$.

REFERENCE EXAMPLE 53

3-Amino-6-bromo-4,5-diethoxycarbonyl-2-phenylpyridine

In 25 ml of ethanol was dissolved 550 mg of 2-bromo-3,4-diethoxycarbonyl-5-nitro-6-phenylpyridine, whereto 0.36 g (5 eq.) of reduced iron was added, followed by heating to 60° C. After 1.5 ml (16 eq.) of acetic acid was added dropwise, the mixture was refluxed for 1 hour.

After the solvent was distilled off, the residue was neutralized with an aqueous solution of sodium hydrogencarbonate, followed by extraction with ethyl acetate. After the precipitate was removed by filtration, the obtained organic layer was washed with water and a saturated aqueous solution of sodium chloride, and dried. Then, the solvent was distilled off. The residue was purified by silica gel column chromatography (eluent:ethyl acetate).

Yield: 390 mg(76%). NMR(CDCl$_3$) δ (ppm): 1.37(3H,t,J=7.2 Hz), 1.44(3H,t,J=7.2 Hz), 4.36(2H,q,J=7.2 Hz), 4.43(2H,q,J=7.2 Hz), 5.94(2H,br.), 7.51(5H,m). IR(KBr) ν: 1730, 1700, 1590, 1405, 1300, 1235 cm$^{-1}$.

EXAMPLE 14

8-Amino-5-bromo-7-phenylpyrido[3,4-d]pyridazine-1,4(2H,3H)dione (L-035)

In a mixture of 1 ml of ethanol and 2 ml of hydrazine monohydrate was dissolved 90 mg of 3-amino-6-bromo-4,5-diethoxycarbonyl-2-phenylpyridine, and the mixture was stirred for 2 hours at room temperature. After the solvent was distilled off, the resulting crystals were collected by filtration with ethanol. Water was added to the crystals, and the mixture was neutralized with 1N hydrochloric acid, the resulting crystals were collected by filtration. The crystals were dissolved in a small volume of methanol. After mixing the methanol solution with silica gel, purification by silica gel column chromatography (eluent:ethyl acetate→ethylacetate/methanol 1:1) was conducted, followed by collection by filtration.

Yield: 21 mg(27%). m.p. 286°–288° (dec.). NMR(DMSO-$d_6$) $\delta$ (ppm): 7.53(3H,m), 7.67(2H,m). IR(KBr) $\nu$: 1645, 1585 cm$^{-1}$.

REFERENCE EXAMPLE 54

3-Amino-6-chloro-4,5-diethoxycarbonyl-2-(4-hydroxyphenyl)pyridine-O-phosphate sodium salt In 4 ml of toluene was suspended 100 mg of 3-amino-6-chloro-4,5-diethoxycarbonyl-2-(4-hydroxyphenyl)-pyridine, and thereto, 0.1 g (5 eq.) of pyridine was added. Then, 2 g (15 eq.) of phosphorus oxychloride was added dropwise under ice-cooling. The mixture was stirred at room temperature for 3 hours. After the solvent was distilled off, the residue was stirred in a mixture of an aqueous solution of sodium hydrogencarbonate and ethyl acetate overnight at room temperature. The aqueous layer was purified with Amberlite®XAD-2 column and Sephadex®LH-20 column chromatography (eluent:water, respectively), followed by crystallization with methanol and diethyl ether.

Yield: 82 mg(64%). $^1$H-NMR(D$_2$O) $\delta$ (ppm): 1.32(3H,t,J=7.1 Hz), 1.37(3H,t,J=7.1 Hz), 4.35(2H,q,J=7.1 Hz), 4.42(2H,q,J=7.1 Hz), 7.40(2H,d,J=8.4 Hz), 7.51(2H,d,J=8.4 Hz). $^{13}$C-NMR(D$_2$O) $\delta$ (ppm): 16.00(2C), 66.17, 66.56, 119.3, 123.71 (2C,Jccop=4.3 Hz, correlated with $^1$H at $\delta$7.40), 129.94, 131.62, 132.43(2C), 134.80, 144.82, 152.94, 158.13(Jcop=5.5 Hz), 168.33, 170.81 IR(KBr) $\nu$: 1740, 1600, 1420, 1310, 1240, 1120, 990 cm$^{-1}$.

EXAMPLE 15

8-Amino-5-chloro-7-(4-hydroxyphenyl)pyrido[3,4-d]pyridazine 1,4(2H,3H)dione O-phosphate sodium salt (L-036)

In 2 ml of hydrazine monohydrate was dissolved 125 mg of 3-amino-6-chloro-4,5-diethoxycarbonyl-2-(4-hydroxyphenyl)pyridine O-phosphate sodium salt, and the solution was stirred at room temperature for 45 minutes. After the solvent was distilled off, 22.5 mg (1.0 eq.) of sodium hydrogencarbonate was added, followed by purification with Sephadex® LH-20 column chromatography (eluent:water). The product was collected by filtration with ethanol.

Yield: 11 mg(10%). NMR(D$_2$O) $\delta$ (ppm): 7.37(2H,d,J=8.8 Hz), 7.56(2H,d,J=8.8 Hz). IR(KBr) $\nu$: 1640, 1580, 1500 cm$^{-1}$. Elemental Analysis: Calcd. (C$_{13}$H$_9$N$_4$O$_6$ClNaP.2H$_2$O) C:35.27; H:2.96; N:12.66; P:7.00. Found C:35.19; H:2.93; N:12.86; P:6.69.

REFERENCE EXAMPLE 55

2-Amino-3,4-diethoxycarbonyl-5-nitro-6-phenylpyridine

In 15 ml of ethanol was dissolved 470 mg of 2-chloro-3,4-diethoxycarbonyl-5-nitro-6-phenylpyridine as obtained in Reference Example 18, whereto a 8.7% ethanol solution of ammonia was added in the total amount of 6 ml. After the mixture was stirred at room temperature for 4 days, the solvent was distilled off and water was added to the residue, followed by extraction with ethyl acetate. The organic layer was washed with water and a saturated aqueous solution of sodium chloride and dried. After the solvent was distilled off, the resulting crystals were collected by filtration with hexane.

Yield: 405 mg(91%). NMR(CDCl$_3$) $\delta$ (ppm): 1.37(3H,t,J=7.2 Hz), 1.39(3H,t,J=7.2 Hz), 4.38(2H,q,J=7.2 Hz), 4.40(2H,q,J=7.2 Hz), 7.48(5H,m).

REFERENCE EXAMPLE 56

3,4-Diethoxycarbonyl-2-fluoro-5-nitro-6-phenylpyridine

In 2 ml of acetic acid was dissolved 100 mg of 2-amino-3,4-diethoxycarbonyl-5-nitro-6-phenylpyridine, and 1.5 ml of 42% hydrofluoroboric acid was added to the solution. The mixture was cooled to $-5°$ C., followed by adding dropwise a solution of 21 mg (1.1 eq) of sodium nitrite dissolved in 0.5 ml of water. Thirty minutes later, the temperature of the mixture was elevated to room temperature and the mixture was neutralized with sodium hydrogencarbonate, followed by extraction with ethyl acetate. After the organic layer was washed with water and a saturated aqueous solution of sodium chloride, and dried. After the solvent was distilled off, the resulting crystals (2-pyridone compound) were collected by filtration with hexane, and washed. The solvent was distilled off from the obtained filtrate, to give an oily substance.

Yield: 52 mg(52%). NMR(CDCl$_3$) $\delta$ (ppm): 1.37(3H,t,J=7.0 Hz), 1.41(3H,t,J=7.2 Hz), 4.43(2H,q,J=7.2 Hz), 4.45(2H,q,J=7.0 Hz), 7.51(5H,m).

REFERENCE EXAMPLE 57

3-Amino-6-fluoro-4,5-diethoxycarbonyl-2-phenylpyridine

In 5 ml of ethanol was dissolved 160 mg of 3,4-diethoxycarbonyl-2-fluoro-5-nitro-6-phenylpyridine, and 120 mg (5 eq.) of reduced iron was added to the solution, followed by addition of 0.5 ml (20 eq.) of acetic acid. After the mixture was refluxed for 30 minutes, the solvent was distilled off. The residue was neutralized with sodium hydrogencarbonate, followed by extraction with ethyl acetate. After the precipitate was removed by filtration, the obtained organic layer was washed with water and a saturated aqueous solution of sodium chloride, and dried. Then, the solvent was distilled off.

Yield: 142 mg(96%). NMR(CDCl$_3$) $\delta$ (ppm): 1.38(3H,t,J=6.8 Hz), 1.41(3H,t,J=6.6 Hz), 4.38(2H,q,J=6.8 Hz), 4.42(2H,q,J=6.6 Hz), 5.54(2H,br.), 7.50(3H,m), 7.64(2H,m).

EXAMPLE 16

8-Amino-5-fluoro-7-phenylpyrido[3,4-d]pyridazine-1,4(2H,3H)dione. (L-037)

In 1 ml of ethanol was dissolved 90 mg of 3-amino-6-fluoro-4,5-diethoxycarbonyl-2-phenylpyridine, followed by addition of 2 ml of hydrazine monohydrate. The mixture was stirred at room temperature for 4 hours. After the solvent was distilled off, the resulting crystals were collected by filtration with ethanol. Water was added to the crystals, and the mixture was neutralized with 1N hydrochloric acid, followed by collection by filtration. A methanol solution of the crystals was mixed with silica gel and purified by silica gel column chromatography (eluent:ethyl acetate→ethyl acetate/methanol 1:1), followed by collection by filtration with water.

Yield: 33 mg(48%). NMR(DMSO-$d_6$) δ (ppm): 7.10(2H,br.), 7.53(3H,m), 7.72(2H,m). IR(KBr) ν: 1660, 1505, 1345, 1325 cm$^{-1}$.

REFERENCE EXAMPLE 58

3,4-Diethoxycarbonyl-5-nitro-6-(3-nitrophenyl)-2-pyridone

In 4.5 ml of conc. sulfuric acid was dissolved 0.72 g of 3,4-diethoxycarbonyl-5-nitro-6-phenyl-2-pyridone as obtained in Reference Example 17, and 0.06 ml of fuming nitric acid was added to the solution under ice-cooling while stirring. After stirring at room temperature for 45 minutes, the resulting mixture was poured into ice water (100 me). The resulting precipitate was filtered off, washed with water and dried to give 0.74 g of the title compound as pale yellow powder.

m.p. 188°–190° C. NMR(CDCl$_3$) δ (ppm): 1.41(3H,t,J=7.0 Hz), 1.42(3H,t,J=7.0 Hz), 4.44(2H,q,J=7.0 Hz), 4.50(2H,q,J=7.0 Hz), 7.63(1H,t,J=8.0 Hz), 7.85(1H,dt,J=1.5,8.0 Hz), 8.39(1H,m), 8.50(1H,t,J=1.5 Hz). IR(KBr) ν: 1755,1660,1535,1350,1290 1275,1210,1105,1035,850,685 cm$^{-1}$. Elemental Analysis: Calcd. ($C_{17}H_{15}N_3O_9$) C:50.38; H:3.73; N:10.37. Found C:50.14; H:3.74; N:10.43.

REFERENCE EXAMPLE 59

2-Chloro-3,4-diethoxycarbonyl-5-nitro-6-(3-nitrophenyl)pyridine

In 2 ml of phosphorus oxychloride was suspended 0.70 g of 3,4-diethoxycaronyl-5-nitro-6-(3-nitrophenyl)-2-pyridone. Then, 0.3 ml of DMF was added to the suspension under ice-coiling, and the mixture was stirred at 100° C. The reaction mixture was poured into ice-water (100 ml). After the mixture was stirred for 30 minutes, it was extracted with ethyl acetate. The extract was washed with an aqueous solution of sodium hydrogencarbonate and an aqueous solution of sodium chloride consecutively, and dried over magnesium sulfate. After the solvent was concentrated to dryness, the residue was subjected to silica gel column chromatography (eluent:hexane/ethyl acetate 4:1). The obtained solidified colorless residue was recrystallized from ethanol to give 0.51 g of the title compound as colorless prisms.

m.p. 90°–91° C. NMR(CDCl$_3$) δ (ppm): 1.36(3H,t,J=7.0 Hz), 1.44(3H, t,J=7.0 Hz), 4.42(2H,q,J=7.0 Hz), 4.49 ( 2H, q,J=7.0 Hz), 7.71(1H,t,J=8.0 Hz), 7.89(1H, dt,J=1.5,8.0 Hz), 8.40(1H,m), 8.53(1H, t,J=1.5 Hz). IR(KBr) ν: 1750,1740,1550,1535,1350,1260, 1235,1020,700 cm$^{-1}$.

REFERENCE EXAMPLE 60

3-Amino-6-chloro-4,5-diethoxycarbonyl-2-(3-aminophenyl)pyridine

In 8 ml of ethanol were suspended 0.37 g of 2-chloro-3,4-diethoxycarbonyl-5-nitro-6-(3-nitrophenyl)pyridine and 0.45 g of reduced iron, and the suspension was heated to 60° C. After 1.9 ml of conc. hydrochloric acid was added thereto, the mixture was heated for 30 minutes under reflux. After the reaction mixture was concentrated, the residue was extracted with ethyl acetate, followed by washing with an aqueous solution of sodium hydrogencarbonate and an aqueous solution of sodium chloride and drying over magnesium sulfate. After the extract was concentrated under reduced pressure, the residue was subjected to silica gel column chromatography (eluent: chloroform/methanol 40:1) to give 0.29 g of the title compound as a yellowish orange viscous oily substance.

NMR(CDCl$_3$) δ (ppm): 1.36(3H,t,J=7.0 Hz), 1.42(3Ht,J=7.0 Hz), 3.81(2H,br.s), 4.36(2H,q,J=7.0 Hz), 4.43(2H,q,J=7.0 Hz), 5.98(2H,br.s), 6.72(1H,ddd,J=1.5,2.0,7.5 Hz), 6.83(1H,dd,J=1.5,2.0 Hz), 6.94(1H,dd,J=1.5,7.5 Hz), 7.24(1H,t,J=7.5 Hz).

EXAMPLE 17

8-Amino-5-chloro-7-(3-aminophenyl)pyrido[3,4-d]pyridazine-1,4(2H,3H)dione (L-038)

To 0.35 g of 3-amino-6-chloro-4,5-diethoxycarbonyl-2-(3-aminophenyl)pyridine was added 7.5 ml of hydrazine monohydrate, and the mixture was stirred at 90° C. for 30 minutes. The reaction mixture was poured into ice water (100 ml), and the mixture was adjusted to pH 6 by adding acetic acid. The resulting precipitate was collected by filtration and washed with water, followed by reprecipitation from DMSO-H$_2$O, to give 0.23 g of the title compound as orange powder.

m.p. 298° C.(dec.). NMR(DMSO-$d_6$) δ (ppm): 5.32(2H,br.s), 6.65(1H,dd,J=1.5,7.5 Hz), 6.80(1H,d,J=7.5 Hz), 6.85(1H,s), 7.17(1H,t,J=7.5 Hz), 7.29(2H,br.s), 10.20–11.60(2H,br.). IR(KBr) ν: 1650,1585,1410,1325,1125 1075,870,810 cm$^{-1}$. Elemental Analysis: Calcd. ($C_{13}H_{10}N_5O_2Cl$) C:51.41; H:3.32; N:23.06. Found C:51.06; H:3.47; N:23.17.

REFERENCE EXAMPLE 61

3,4-Diethoxycarbonyl-5-nitro-6-phenyl-2-pyridone

In 150 ml of acetic acid was dissolved 21 g of 2-amino-3,4-diethoxycarbonyl-6-phenylpyridine hydrochloride as obtained in Reference Example 15, and 18 ml of fuming nitric acid (d=1.58) was added dropwise to the solution at room temperature while stirring. Then, the mixture was stirred at 100° C. for 2 hours. The reaction mixture was cooled to room temperature, whereafter 300 ml of water was added. The mixture was ice-cooled for 30 minutes. The resulting crystals were collected by filtration, washed with water and dried, to give 15 g of the title compound. The physical data of the compound were in accord with those of the compound as obtained by a different synthetic method in Reference Example 17.

REFERENCE EXAMPLE 62

2-Chloro-3,4-diethoxycarbonyl-5-nitro-6-phenylpyridine

In 6.5 ml of phosphorus oxychloride was dissolved 2.5 g of 3,4-diethoxycarbonyl-5-nitro-6-phenyl-2pyridone, followed by addition of 1 ml of DMF. The mixture was heated at 100° C. for 30 minutes. After the reaction mixture was concentrated under reduced pressure, an aqueous solution of sodium hydrogencarbonate was added to the residue for neutralization, followed by extraction with ethyl acetate. The organic layer was washed with water and a saturated aqueous solution of sodium chloride and dried over magnesium sulfate. After the solvent was distilled off, the residue was subjected to silica gel column chromatography (eluent:ethyl acetate/hexane 1:2), to give 1.9 g of the title compound as yellow needles.

m.p. 65°–66° C. NMR(CDCl$_3$) δ (ppm): 1.35(3H,t,J=7.2 Hz), 1.42(3H,t,J=7.2 Hz), 4.44(4H,q,J=7.2 Hz), 7.52(5H,m). IR(KBr) ν: 2990,1750,1580,1550 cm$^{-1}$.

REFERENCE EXAMPLE 63

3-Amino-4,5-diethoxycarbonyl-6-(imidazol-1-yl)-2-phenylpyridine

A mixture of 0.379 g of 2-chloro-3,4-diethoxycarbonyl-5-nitro-6-phenylpyridine, 0.21 g of imidazole and 15 ml of chloroform was heated under reflux for 8 hours. After the reaction mixture was concentrated, the residue was extracted with ethyl acetate. The organic layer was washed with water and a saturated aqueous solution of sodium chloride and dried over sodium sulfate. After the solvent was distilled off, 5 ml of acetic acid and 0.5 g of reduced iron were added to the residue, and the mixture was stirred at room temperature for 4 hours. After an aqueous solution of sodium hydrogencarbonate was added for neutralization, extraction with ethyl acetate was conducted. The organic layer was washed with water and a saturated aqueous solution of sodium chloride and dried over sodium sulfate, followed by filtration with a small amount of silica gel. The filtrate was concentrated under reduced pressure, to give 0.342 g of the title compound as a yellow oily substance.

NMR(CDCl$_3$) δ (ppm): 1.18(3H,t,J=7.2 Hz), 1.37(3H,t,J=7.2 Hz), 4.20(2H,q,J=7.2 Hz), 4.39(2H,q,J=7.2 Hz), 6.02(2H,br.s), 7.12(1H,s), 7.24(1H,s), 7.40–7.75(5H,m), 7.80(1H,s).

EXAMPLE 18

8-Amino-5-(imidazol-1-yl)-7-phenylpyrido[3,4-d]pyridazine-1,4(2H,3H)dione (L-039)

In 10ml of ethanol was dissolved 0.342 g of 3-amino-4,5-diethoxycarbonyl-6-(imidazol-1-yl)-2-phenylpyridine, and 0.5 ml of hydrazine monohydrate was added to the solution. The mixture was heated under reflux for 7 hours. After the reaction mixture was concentrated, the residue was acidified with acetic acid. The resulting precipitate was collected with. filtration and washed with water, followed by reprecipitation from DMF/H$_2$O, to give 0.2 g of the title compound as yellow powder.

m.p. 320° C.(dec.). NMR(DMSO-d$_6$) δ (ppm): 6.93(1H,s), 7.38(1H,s), 7.40–7.80(5H,m), 7.81(1H,s), 11.20(1H,br.s), 11.95(1H,br.s). IR(KBr) ν: 1645,1580,1540,1090 cm$^{-1}$. Elemental Analysis: Calcd. (C$_{16}$H$_{12}$N$_6$O$_2$.0.2H$_2$O) C:59.33; H:3.86; N:3.86; N:25.95. Found C:59.28; H:3.84; N:25.92.

REFERENCE EXAMPLE 64

3,4-Diethoxycarbonyl-5-nitro-6-phenyl-2-(1,2,4-triazol-1-yl)pyridine

A mixture of 0.379 g of 2-chloro-3,4-diethoxycarbonyl-5-nitro-6-phenylpyridine, 0.2 g of (1H-1,2,4-triazole, 0.2 ml of pyridine and 15 ml of 1,2-dichloroethane was reacted at 80° C. for 18 hours. After the reaction mixture was concentrated, the concentrate was extracted with ethyl acetate. The extract was washed with water and a saturated aqueous solution of sodium chloride and dried over sodium sulfate. After the solvent was distilled off, the residue was subjected to silica gel column chromatography (eluent:dichloromethane/ethyl acetate 4:1), to give 0.19 g of the title compound as yellow crystals.

NMR(CDCl$_3$) δ (ppm): 1.33(3H,t,J=7.2 Hz), 1.37(3H,t,J=7.2 Hz), 4.42(2H,q,J=7.2 Hz), 4.44(2H,q,J=7.2 Hz), 7.44–7.70(5H,m), 8.12(1H,s), 9.12(1H,s).

REFERENCE EXAMPLE 65

3-Amino-4,5-diethoxycarbonyl-2-phenyl-6-(1,2,4-triazol-1-yl)pyridine

In 25 ml of ethyl acetate was dissolved 0.35 g of 3,4-diethoxycarbonyl-5-nitro-6-phenyl-2-(1,2,4-triazol-1-yl)pyridine, whereto 0.2 g of 10% Pd-C (50% wet) was added. The mixture was stirred in a stream of hydrogen at room temperature for 2.5 hours. After the catalyst was removed by filtration, the filtrate was concentrated. The residue was subjected to silica gel column chromatography (eluent:chloroform/ethyl acetate 4:1), to give 0.215 g of the title compound.

NMR(CDCl$_3$) δ (ppm): 1.28(3H,t,J=7.2 Hz), 1.38(3H,t,J=7.2 Hz), 4.33(2H,q,J=7.2 Hz), 4.40(2H,q,J=7.2 Hz), 5.89(2H,br.s), 7.40–7.70(5H,m), 8.01(1H,s), 8.77(1H,s).

EXAMPLE 19

8-Amino-7-phenyl-5-(1,2,4-triazol-1-yl)pyrido[3,4-d]pyridazine-1,4(2H,3H)dione (L-040)

In 15 ml of ethanol was dissolved 0.215 g of 3-amino-4,5-diethoxycarbonyl-2-phenyl-6-(1,2,4-triazol-1-yl)pyridine, whereto 1 ml of hydrazine monohydrate was added. The mixture was heated under reflux for 7 hours. After cooling, the resulting yellow crystals were collected by filtration and washed with ethanol. The crystals were suspended in 20 ml of water and the suspension was acidified by addition of 1 ml of acetic acid. Thereafter, the crystals were collected by filtration, washed with water and dried to give 0.11 g of the title compound.

m.p.290°–292° C.(dec.). NMR(DMSO-d$_6$) δ (ppm): 7.40–8.10(7H,m), 8.08(1H,s), 8.74(1H,s), 10.80–12.20(2H,br.). IR(KBr)ν: 1650, 1600, 1590, 1510, 1310, 1290, 1130 cm$^{-1}$. Elemental Analysis: Calcd. (C$_{15}$H$_{11}$N$_7$O$_2$) C:55.52; H:3.54; N:31.08. Found C:55.48; H:3.45; N:31.28.

REFERENCE EXAMPLE 66

3,4-Diethoxycarbonyl-5-nitro-6-phenyl-2-(tetrazol-1-yl)pyridine

A mixture of 1.52 g of 2-chloro-3,4-diethoxycarbonyl-5-nitro-6-phenylpyridine, 0.84 g of H-tetrazole, 0.84 ml of diisopropylethylamine and 50 ml of 1,2-dichloroethane was reacted at 90° C. for 24 hours. After the reaction mixture was adjusted to pH 2 by adding dil. hydrochloric acid, the organic layer was washed with water and a saturated aqueous solution of sodium chloride and dried over sodium sulfate. After concentration, the residue was subjected to silica gel column chromatography with chloroform as the eluent, to give 0.36 g of the title compound as yellow crystals.

NMR(CDCl$_3$) δ (ppm): 1.31(3H,t,J=7.4 Hz), 1.38(3H,t,J=7.4 Hz), 4.43(2H,q,J=7.4 Hz), 4.47(3H,t,J=7.4 Hz), 7.45–7.85(5H,m), 9.43(1H,s).

REFERENCE EXAMPLE 67

3-Amino-4,5-diethoxycarbonyl-2-phenyl-6-(tetrazol-1-yl)pyridine

A mixture of 0.36 g of 3,4-diethoxycarbonyl-5-nitro-6-phenyl-2-(tetrazol-1-yl)pyridine, 0.3 g of 10% Pd-C (50% wet) and 30 ml of ethyl acetate was stirred at room temperature for 2 hours in a stream of hydrogen. After the catalyst was filtered off, the reaction mixture was subjected to silica gel column chromatography with chloroform as the eluent, to give 0.172 g of the title compound.

NMR(CDCl$_3$) δ (ppm): 1.27(3H,t,J=7.1 Hz), 1.39(3H,t,J=7.1 Hz), 4.33(2H,q,J=7.1 Hz), 4.41(2H,q,J=7.1 Hz), 6.12(2H,br.s), 7.50–7.70(5H,m), 9.14(1H,s).

EXAMPLE 20

8-Amino-7-phenyl-5-(tetrazol-1-yl)pyrido[3,4-d]pyridazine-1,4(2H,3H)dione (L-041)

In 2 ml of ethanol was dissolved 0.172 g of 3-amino-4,5-diethoxycarbonyl-2-phenyl-6-(tetrazol-1-yl)pyridine, whereto 1 ml of hydrazine monohydrate was added. The mixture was reacted at 90° C. for 2 hours. After 15 ml of ethanol was added, the mixture was cooled. The precipitate was collected by filtration and washed with ethanol. The thus-obtained precipitate was dissolved in 20 ml of hot water, and 0.7 ml of acetic acid was added. The mixture was cooled, and the resulting precipitate was collected by filtration, washed and dried, to give 0.11 g of the title compound as yellow crystals.

m.p.190° C.(dec.). NMR(DMSO-d$_6$) δ (ppm): 7.40–7.80(5H,m), 7.30–8.30(2H,br.), 9.71(1H,s), 10.80–12.40(2H,br.). IR(KBr)ν: 1650, 1590, 1560, 1510, 1300, 1090 cm$^{-1}$. Elemental Analysis: Calcd. (C$_{14}$H$_1$N$_8$O$_2$.0.8H$_2$O) C:49.94; H:3.47; N:33.28. Found. C:50.07; H:3.23; N:33.27.

REFERENCE EXAMPLE 68

3,4-Diethoxycarbonyl-5-nitro-6-phenyl-2-(p-tolylsulfonyl)pyridine

A mixture of 0.379 g of 2-chloro-3,4-diethoxycarbonyl-5-nitro-6-phenylpyridine, 0.5 g of sodium p-toluenesulfinate tetrahydrate and 15 ml of ethanol was heated under reflux for 3 hours. After concentration, the concentrate was extracted with ethyl acetate. The extract was washed with a saturated aqueous solution of sodium chloride, and dried over sodium sulfate. After the solvent was distilled off, the residue was subjected to silica gel column chromatography with n-hexane/ethyl acetate (4:1) as the eluent. The eluate was concentrated to give crystals. The obtained crystals were recrystallized from the same solvent, to give 0.289 g of the title compound as colorless needles.

m.p.115°–117° C. NMR(CDCl$_3$) δ (ppm): 1.34(3H,t,J=7.2 Hz), 1.48(3H,t,J=7.2 Hz), 2.46(3H,s), 4.40(2H,q,J=7.2 Hz), 4.56(2H,q,J=7.2 Hz), 7.30–7.60(5H,m), 7.34(2H,d,J=8.2 Hz), 7.98(2H,d,J=8.2 Hz). IR(KBr)ν: 1740, 1730, 1580, 1550, 1330, 1300, 1270, 1230, 1160, 1100, 1010 cm$^{-1}$. Elemental Analysis: Calcd. (C$_{24}$H$_{22}$N$_2$O$_8$S) C:57.83; H:4.45; N:5.62. Found C:57.77; H:4.31; N:5.42

REFERENCE EXAMPLE 69

3-Amino-4,5-diethoxycarbonyl-2-phenyl-6-(p-tolylsulfonyl)pyridine

In 10 ml of ethanol was suspended 0.35 g of 3,4-diethoxycarbonyl-5-nitro-6-phenyl-2-(p-tolylsulfonyl)pyridine, whereto 2 ml of acetic acid and 0.15 g of reduced iron were added. The mixture was stirred at 80° C. for 4.5 hours. After ethanol was distilled off, the residue was neutralized with an aqueous solution of sodium hydrogencarbonate, followed by extraction with ethyl acetate. The organic layer was washed with a saturated aqueous solution of sodium chloride and dried over sodium sulfate, followed by concentration under reduced pressure. The residue was subjected to silica gel flash column chromatography with chloroform/ethyl acetate (4:1) as the eluent, to give 0.144 g of the title compound.

NMR(CDCl$_3$) δ (ppm): 1.39(3H,t,J=7.2 Hz), 1.48(3H,t,J=7.2 Hz), 2.40(3H,s), 4.37(2H,q,J=7.2 Hz), 4.53(2H,q,J=7.2 Hz), 6.50(2H,s), 7.26(2H,d,J=8.2 Hz), 7.49(5H,m), 7.94(2H,q,J=8.2 Hz).

EXAMPLE 21

8-Amino-7-phenyl-5-(p-tolylsulfonyl)pyrido[3,4-d]pyridazine-1,4(2H,3H)dione (L-042)

To 0.251 g of 3-amino-4,5-diethoxycarbonyl-2-phenyl-6-(p-tolylsulfonyl)pyridine were added 2 ml of hydrazine monohydrate and 2 ml of ethanol, and the mixture was stirred at 90° C. for 2 hours. After ethanol was added, the mixture was cooled. The resulting precipitate was collected by filtration and washed with ethanol. The thus obtained precipitate was suspended in 30 ml of water, and 2 ml of acetic acid was added thereto. After the mixture was heated, it was cooled. The resulting precipitate was collected by filtration, washed with water and dried to give 0.15 g of the title compound.

m.p.310°–314° C.(dec.). NMR(DMSO-d$_6$) δ (ppm): 2.47(3H,s), 7.10–7.50(5H,m), 7.42(2H,d,J=8.4 Hz), 7.70(2H,d,J=8.4 Hz), 12.00(2H,br.). IR(KBr)ν: 1650, 1580, 1315, 1140 cm$^{-1}$. Elemental Analysis: Calcd. (C$_{20}$H$_{16}$N$_4$O$_4$S) C:58.81; H:3.95; N:13.72. Found C:58.67; H:4.08; N:13.62.

REFERENCE EXAMPLE 70

2-Amino-3,4-diethoxycarbonyl-5-nitro-6-(4-nitrophenyl)pyridine

In 12 ml of conc. sulfuric acid was dissolved 2.0 g of 2-amino-3,4-diethoxycarbonyl-6-phenylpyridine (as was obtained by neutralizing the hydrochloride obtained in Reference Example 15), and 0.58 ml of fuming nitric acid was added to the solution while stirring under ice-cooling. After the mixture was stirred at room temperature for 1 hour, the reaction mixture was poured into ice-water (300 ml). The resulting precipitate was collected by filtration and washed with water.

The obtained precipitate was dissolved in ethyl acetate and washed with an aqueous solution of sodium hydrogencarbonate and an aqueous solution of sodium chloride consecutively and dried over magnesium sulfate. After concentration under reduced pressure, the residue was subjected to silica gel column chromatography (eluent:hexane/ethyl acetate 3:1), to give 0.95 g of the title compound as yellow crystals.

m.p.148°–150° C. NMR(CDCl$_3$) δ (ppm): 1.38(3H,t,J=7.0 Hz), 1.39(3H,t,J=7.0 Hz), 4.40(2H,q,J=7.0 Hz), 4.41(2H,q,J=7.0 Hz), 7.62(1H,s), 6.50–7.50(2H,br.), 7.65(2H,d,J=9.0 Hz), 8.29(2H,d,J=9.0 Hz). IR(KBr)ν: 1750, 1710, 1600, 1565, 1525, 1440, 1350, 1330, 1300, 1265, 1235, 1110, 1020, 705 cm$^{-1}$. Elemental Analysis: Calcd. (C$_{17}$H$_{16}$H$_4$O$_8$) C:50.50; H:3.99; N:13.86. Found C:50.29; H:3.76; N:13.82.

REFERENCE EXAMPLE 71

2-Chloro-3,4-diethoxycarbonyl-5-nitro-6-(4-nitrophenyl)pyridine

In 20 ml of acetic acid was suspended 3.1 g of 2-amino-3,4-diethoxycarbonyl-5-nitro-6-(4-nitrophenyl)pyridine, whereto 3 ml of fuming nitric acid was added while stirring under ice-cooling. Then, the mixture was reacted at 110° C. for 3 hours. The reaction mixture was poured into ice water (300 ml), and the resultant precipitate was collected by filtration and washed with water. The obtained precipitate was dissolved in ethyl acetate, washed with an aqueous solution of sodium hydrogencarbonate and an aqueous solution of sodium chloride, and dried over magnesium sulfate. The solvent was distilled off under reduced pressure, whereby 2.94 g of the title compound was obtained as yellowish orange powder.

NMR(CDCl$_3$) δ (ppm): 1.30–1.50(6H,m), 4.30–4.50(4H,m) 7.50–7.60(2H,br.) 8.15–8.25(2H,br.).

The crude product as obtained in the above manner (2.90 g) was suspended in 9 ml of phosphorus oxychloride, whereto 1.2 ml of DMF was added. The mixture was stirred at 100° C. for 1 hour. The reaction mixture was poured into ice water (200 ml) and the mixture was stirred for 30 minutes, followed by extraction with ethyl acetate. The ethyl acetate layer was washed with an aqueous solution of sodium hydrogencarbonate and an aqueous solution of sodium chloride and dried over magnesium sulfate, followed by concentration under reduced pressure. The residue was subjected to silica gel column chromatography (eluent:hexane/ethyl acetate 6:1), to give 0.95 g of the title compound as a colorless viscous oily substance.

NMR(CDCl$_3$) δ (ppm): 1.35(3H,t,J=7.0 Hz), 1.43(3H,t,J=7.0 Hz), 4.42(2H,q,J=7.0 Hz), 4.49(2H,q,J=7.0 Hz), 7.78(2Hd,J=9.0 Hz), 8.35(2H,d,J=9.0 Hz). IR(neat)ν: 2980, 1740, 1580, 1550, 1530, 1350, 1300, 1260, 1230, 1130, 1095, 1015, 860, 830, 735, 700 cm$^{-1}$.

REFERENCE EXAMPLE 72

3-Amino-6-chloro-4,5-diethoxycarbonyl-2-(4-aminophenyl)pyridine

In 20ml of ethanol were suspended 0.91 g of 2-chloro-3,4-diethoxycarbonyl-5-nitro-6-(4-nitrophenyl)pyridine and 1.11 g of reduced iron, and the suspension was heated to 60° C. After 4.7 ml of conc. hydrochloric acid was added, the mixture was heated under reflux for 20 minutes. After the reaction mixture was concentrated, extraction with ethyl acetate was conducted. The extract was washed with an aqueous solution of sodium hydrogencarbonate and an aqueous solution of sodium chloride consecutively, and dried over magnesium sulfate. After concentration, the residue was subjected to silica gel column chromatography (eluent:chloroform/methanol 40:1), to give 0.58 g of the title compound as yellow prisms.

m.p.137° C. NMR(CDCl$_3$) δ (ppm): 1.37(3H,t,J=7.0 Hz), 1.42(3H,t,J=7.0 Hz), 3.84(2H,br.s), 4.36(2H,q,J=7.0 Hz), 4.42(2H,q,J=7.0 Hz), 5.95(2H,s), 6.77(2H,d,J=8.5 Hz), 7.44(2H,d,J=8.5 Hz). IR(KBr)ν: 1735, 1700, 1610, 1520, 1405, 1305, 1235, 1180, 1105, 1065, 1025, 835 cm$^{-1}$.

EXAMPLE 22

8-Amino-5-chloro-7-(4-aminophenyl)pyrido[3,4-d]pyridazine-1,4(2H,3H)dione (L-043)

To 0.30 g of 3-amino-6-chloro-4,5-diethoxycarbonyl-2-(4-aminophenyl)pyridine was added 6 ml of hydrazine monohydrate, and the mixture was heated at 90° C. for 30 minutes. The reaction mixture was poured into 150 ml of ice-water and the mixture was adjusted to pH 6 with acetic acid. The resultant precipitate was collected by filtration, and washed with water, followed by reprecipitation from DMSO/H$_2$O, whereby 0.21 g of the title compound was obtained as orange powder.

m.p. >300° C. NMR(DMSO-d$_6$) δ (ppm): 5.53(2H,br.s), 6.68(2H,d,J=8.5 Hz), 7.29(2H,br.s), 7.44(2H,d,J=8.5 Hz), 11.30–11.90(2H,br.). IR(KBr)ν: 1625, 1605, 1580, 1400, 1290, 1180, 1120, 1070, 870, 835 cm$^{-1}$. Elemental Analysis: Calcd. (C$_{13}$H$_{10}$N$_5$O$_2$Cl.¼H$_2$O) C:50.66; H:3.43; N:22.72. Found C:50.70; H:3.51; N:22.85.

REFERENCE EXAMPLE 73

3,4-Diethoxycarbonyl-5-nitro-6-phenyl-2-sulfopyridine

A solution of 0.28 g of sodium sulfite in 7 ml of water was added to a solution of 0.70 g of 2-chloro-3,4-diethoxycarbonyl-5-nitro-6-phenylpyridine in 7 ml of ethanol, and the mixture was heated under reflux for minutes. After the reaction mixture was concentrated, the concentrate was acidified with 1N HCl, followed by extraction with ethyl acetate. The extract was washed with an aqueous solution of sodium chloride and dried over magnesium sulfate. After concentration to dryness under reduced pressure, the residue was recrystallized from chloroform/ether, to give 0.47 g of white crystals.

m.p.187°–190° C. NMR(CDCl$_3$) δ (ppm): 1.16(3H,t,J=7.0 Hz), 1.27(3H,t,J=7.0 Hz), 4.25(2H,q,J=7.0 Hz), 4.32(2H,q,J=7.0 Hz), 7.23(3H,br.s), 7.35(2H,br.s).

REFERENCE EXAMPLE 74

3-Amino-4,5-diethoxycarbonyl-2-phenyl-6-sulfopyridine

A mixture of 0.34 g of 3,4-diethoxycarbonyl-3-nitro-2-phenyl-6-sulfopyridine, 0.41 g of reduced iron and 7 ml of ethanol was heated to 60° C., and then 0.5 ml of conc. hydrochloric acid was added. The mixture was heated under reflux for 20 minutes. After the reaction mixture was concentrated to dryness, the residue was subjected to silica gel column chromatography (eluent:chloroform/methanol 5:1), to give 0.24 g of the title compound as pale yellow crystals.

m.p.220° C.(dec). NMR(DMSO-d$_6$) δ (ppm): 1.26(6H,t,J=7.0 Hz), 4.16(2H,q,J=7.0 Hz), 5.94(2H,s), 7.45–7.60(5H,m). IR(KBr)ν: 1720, 1600, 1420, 1385, 1320, 1250, 1200, 1085, 1045, 665, 605 cm$^{-1}$.

EXAMPLE 23

8-Amino-5-sulfo-7-phenylpyrido[3,4-d]pyridazine-1,4(2H,3H)dione (L-044)

To 0.184 g of 3-amino-4,5-diethoxycarbonyl-2-phenyl-6-sulufopyridine was added 9 ml of hydrazine monohydrate, and the mixture was reacted at 90° C. for 30 minutes. After the reaction mixture was concentrated under reduced pressure, ethanol was added. The resultant precipitate was collected by filtration, and subjected to Sephadex ® LH-20 column chromatography (eluent:water). The objective fraction was lyophilized to give 0.059 g of the title compound as yellow powder.

m.p.175°–180° C.(dec.). NMR(DMSO-d$_6$) δ (ppm): 2.80–5.20(ca.10H,br.), 7.40–7.60 (3H,m), 7.65–7.75(2H,m). IR(KBr)ν: 1650, 1585, 1325, 1225, 1170, 1075, 1030, 635, 580 cm$^{-1}$.

REFERENCE EXAMPLE 75

3,4-Diethoxycarbonyl-2-mercapto-5-nitro-6-phenylpyridine

In 10 ml of methanol was dissolved 0.27 g of 2-chloro-3,4-diethoxycarbonyl-5-nitro-6-phenylpyridine, whereto 0.14 g of sodium hydrosulfide n-hydrate was added. The mixture was stirred at room temperature for minutes. After the reaction mixture was concentrated to dryness, it was acidified with 1N HCl, followed by extraction with ethyl acetate. The organic layer was washed with an aqueous solution of sodium chloride and dried over magnesium sulfate, followed by concentration to dryness, whereby 0.31 g of the title compound was obtained as orange crystals.

m.p.129°–132° C. NMR(CDCl$_3$) δ (ppm): 1.36(3H,t,J=7.0 Hz), 1.41(3H,t,J=7.0 Hz), 4.39(2H,q,J=7.0 Hz), 4.44(2H,q,J=7.0 Hz), 7.40–7.60(5H,m). IR(KBr)ν: 1740, 1570, 1525, 1345, 1270, 1235, 1215, 1125, 1020, 705 cm$^{-1}$.

REFERENCE EXAMPLE 76

3-Amino-4,5-diethoxycarbonyl-6-mercapto-2-phenylpyridine

A mixture of 0.30 g of 3,4-diethoxycarbonyl-2-mercapto-5-nitro-6-phenylpyridine, 0.41 g of reduced iron and 7 ml of ethanol was heated to 60° C., followed by addition of 1.7 ml of conc. hydrochloric acid. The mixture was heated under reflux for 30 minutes. After the reaction mixture was concentrated, the concentrate was extracted with ethyl acetate. The extract was washed with an aqueous solution of sodium chloride and dried over magnesium sulfate. The concentrate was subjected to silica gel column chromatography with chloroform as the eluent, to give 0.21 g of the title compound as a yellowish orange viscous oily substance.

NMR(CDCl$_3$) δ (ppm): 1.33(3H,t,J=7.0 Hz), 1.34(3H,t,J=7.0 Hz), 4.31(2H,q,J=7.0 Hz), 4.32(2H,q,J=7.0 Hz), 5.84(2H,s), 7.35–7.40(3H,m), 7.40–7.50(2H,m). IR(KBr)ν: 1725, 1590, 1405, 1305, 1235, 1110, 1070, 1030, 710 cm$^{-1}$.

EXAMPLE 24

8-Amino-5-mercapto-7-phenylpyrido[3,4-d]pyridazine-1,4(2H,3H)dione (L-045)

To 0.21 g of 3-amino-4,5-diethoxycarbonyl-6-mercapto-2-phenylpyridine was added 6 ml of hydrazine monohydrate, and the mixture was heated at 90° C. for 15 minutes. The reaction mixture was poured into ice water, and the mixture was acidified with acetic acid. The resulting precipitate was collected by filtration, to give 53 mg of brown powder. The filtrate was subjected to Sephadex ® LH-20 column chromatography with water as the eluent, to give 34 mg of brown powder. The both powder were combined and subjected to silica gel column chromatography (eluent:chloroform/methanol 5:1) to give 47 mg of the title compound.

m.p.245°–248° C.(dec.). NMR(DMSO-d$_6$) δ (ppm): 4.90(2H,br.s), 5.77(1H,s), 7.55–7.60(3H,m), 7.60–7.70(2H,m). IR(KBr)ν: 1705, 1620, 1580, 1520, 1415, 1260 cm$^{-1}$. Elemental Analysis: Calcd. (C$_{13}$H$_{10}$N$_4$O$_2$S.$\frac{1}{2}$H$_2$O) C:52.87; H:3.75; N:18.97. Found C:52.96; H:3.25; N:18.43.

REFERENCE EXAMPLE 77

3,4-Dimethoxycarbonyl-2-methoxy-6-methyl-5-nitropyridine

In 5 ml of methanol was dissolved 0.5 g of 2-chloro-3,4-diethoxycarbonyl-6-methyl-5-nitropyridine as was obtained in Reference Example 34, whereto 0.37 ml (1.2 eq.) of a 28% methanol solution of sodium methoxide was added. The mixture was stirred at room temperature for 1.5 hours. After the solvent was distilled off, water was added, followed by extraction with ethyl acetate. After the organic layer was washed with water and a saturated aqueous solution of sodium chloride and dried, the solvent was distilled off to give crystals.

Yield: 0.36 g (79.7%) NMR(CDCl$_3$) δ (ppm): 2.66(3H,s), 3.90(6H,s), 4.07(3H,s).

REFERENCE EXAMPLE 78

3-Amino-4,5-dimethoxycarbonyl-6-methoxy-2-methylpyridine

In 5 ml of ethyl acetate was dissolved 350 mg of 3,4-dimethoxycarbonyl-2-methoxy-6-methyl-5-nitropyridine, and 300 mg of 10% Pd-C (50% wet) was added to the solution. Catalytic reduction reaction was conducted for 4.5 hours. After the reaction mixture was dried over magnesium sulfate, the solvent was distilled off to afford an oily product.

Yield: 280 mg (89.4%). NMR(CDCl$_3$) δ (ppm): 2.40(3H,s), 3.86(3H,s), 3.88(3H,s), 3.90(3H,s), 4.93(2H,br.).

EXAMPLE 25

8-Amino-5-methoxy-7-methylpyrido[3,4-d]pyridazine-1,4(2H,3H)dione (L-018)

In 8 ml of methanol was dissolved 280 mg of 3-amino-4,5-dimethoxycarbonyl-6-methoxy-2-methylpyridine, and then 0.54 ml (10 eq.) of hydrazine monohydrate was added to the solution. The mixture was refluxed. The resulting crystals were collected by filtration and washed with methanol. The crystals were suspended in water, and the suspension was acidified with hydrochloric acid. The crystals were collected by filtration and washed with water.

Yield: 46 mg (18.8%). m.p. 285°–287° (dec.). NMR(DMSO-d$_6$) δ (ppm): 2.37(3H,s), 3.87(3H,s), 6.59(2H,br.). IR(KBr) ν: 3460, 3340, 1650, 1630 cm$^{-1}$. Elemental Analysis: Calcd. (C$_9$H$_{10}$N$_4$O$_3$): C: 48.65; H:4.54; N:25.21. Found C.48.70; H,4.53; N,24.95.

EXAMPLE 26

8-Amino-5-hydroxy-7-phenylpyrido[3,4-d]pyridazine-1,4(2H,3H)dione (L-007)

To 50 mg of 3-amino-4,5-diethoxycarbonyl-6-hydroxy-2-phenylpyridine as obtained in Reference Example 29 was added 1 ml of hydrazine monohydrate. The mixture was heated at 100° C. in a stream of nitrogen for 1 hour. Under ice-cooling, water was added to the reaction mixture, followed by neutralization with hydrochloric acid to adjust it to pH 5. The resulting yellow crystalline precipitate was collected by filtration.

Yield: 37 mg (90.5%). m.p. >300° C. NMR(DMSO-$d_6$) $\delta$ (ppm): 5.97(2H,br.), 7.53(5H,m). IR(KBr) $v$: 3480, 3350, 2970–2900, 1670, 1640, 1575, 1565, 1255, 800 cm$^{-1}$. Elemental Analysis: Calcd. ($C_{13}H_{10}N_4O_3.0.4-H_2O$) C:56.28; H:3.78; N:20.19. Found C:56.43; H:3.58; N:20.33.

EXAMPLE 27

8-Amino-5-dimethylamino-7-phenylpyrido[3,4-d]pyridazine-1,4(2H,3H)dione (L-019)

To 250 mg of 3-amino-4,5-diethoxycarbonyl-6-dimethylamino-2-phenylpyridine as obtained in Reference Example 31 was added 5 ml of hydrazine monohydrate. The mixture was heated at 100°–110° C. for 1.5 hours. After solvent was distilled off, water was added to the residue and the mixture was adjusted to pH 3. The precipitate was collected by filtration. With 1N sodium hydroxide, it was converted to the sodium salt, which was collected by filtration.

Yield: 106 mg (47.5%). m.p. >300° C. NMR(DMSO-$d_6$) $\delta$ (ppm): 2.79(6H,s), 7.03(2H,br.), 7.42(3H,m), 7.84(2H,d,J=8.4 Hz). IR(KBr) $v$: 3030, 1655, 1585 cm$^{-1}$. Elemental Analysis: Calcd. ($C_{15}H_{14}N_5O_2Na$) C:56.43; H:4.42; N:21.93. Found C,56.25; H,4.49; N,21.72.

EXAMPLE 28

Sodium salt of 8-amino-5-chloro-7-phenylpyrido[3,4-d]pyridazine-1,4(2H,3H)dione (L-012)

1.50 g of 8-Amino-5-chloro-7-phenylpyrido[3,4-d]pyridazine-1,4-(2H,3H)dione (L-012) was dissolved in 50 ml of 1N aqueous solution of sodium hydroxide with stirring.

A pale yellow sodium salt in the form of needles was quickly separated out. The crystals were filtered off, washed with a small amounts of 1N aqueous solution of sodium hydroxide and ethanol, and dried in vacuo to give 1.48 g of L-012 sodium salt.

m.p. >300° C. NMR(DMSO-$d_6$) $\delta$ (ppm): 7.35–7.55(3H,m), 7.65–7.70(2H,m), 10.50(1H,br,s). IR(KBr) $v$: 1650, 1550, 1455, 870 cm$^{-1}$. Elemental Analysis: Calcd. ($C_{13}H_8N_4O_2ClNa$) C:50.26; H:2.60; N:18.03. Found C:49.91; H:2.35; N: 17.63

EXAMPLE 29

Sandwich Enzyme Immunoassay Method Utilizing Chemiluminescent Detection Means (II)

Assay of hbFGF in human serum was conducted using an immunoplate for EIA.

[1] Preparation of antibody-sensitized plate

Equal amounts of MAb52 and MAb98 were mixed and diluted with 0.1 M carbonate buffer (pH 9.6) to a total protein concentration of 50 μg/ml. The resulting solution was poured in an amount of 100 μl/well into an immunoplate for EIA (Micro Fluor "N" Plate, Dynatech), followed by standing at 4° C. overnight to sensitize the antibody to the plate. After washing the plate with 0.01 M phosphate buffer (pH 7.0) containing 0.15 M NaCl, 300 μl of 0.01 M phosphate buffer (pH 7.0) containing 25% Block-Ace® and 0.15 M NaCl was poured into each well. Then, the plate was stored in a chilled place until its use.

[2] Assay of bFGF in human serum (a) Reagents (1) Enzyme-labelled antibody obtained in Example 9 (3H3-HRP), (2) Antibody-sensitized microtiter plate obtained in (1) above, (3) Recombinant human bFGF (rhbFGF), (4) Buffer A[0.02 M phosphate buffer (pH 7.0) containing 0.15 M NaCl], Buffer B[0.02 M phosphate buffer (pH 7.0) containing 25% Block-Ace®, 0.15 M NaCl and 100 μg/ml heparin], Buffer C [Buffer B containing 1 mg/ml mouse IgG]

(5) Solution of L-012 for chemiluminescence [Tris-HCl buffer (pH 7.5) containing 100 μM L-012, 50 μM 4-(4-hydroxyphenyl)thiazole and 25 μM EDTA]

(6) bFGF-zero serum (bFGF free serum which was obtained by applying human pooled-sera to affinity column with MAb98 immobilized)

(7) Inactivated HRP (which was obtained by autoclaving HRP at 121° C. for 30 minutes)

(b) Assay

Figure 3:
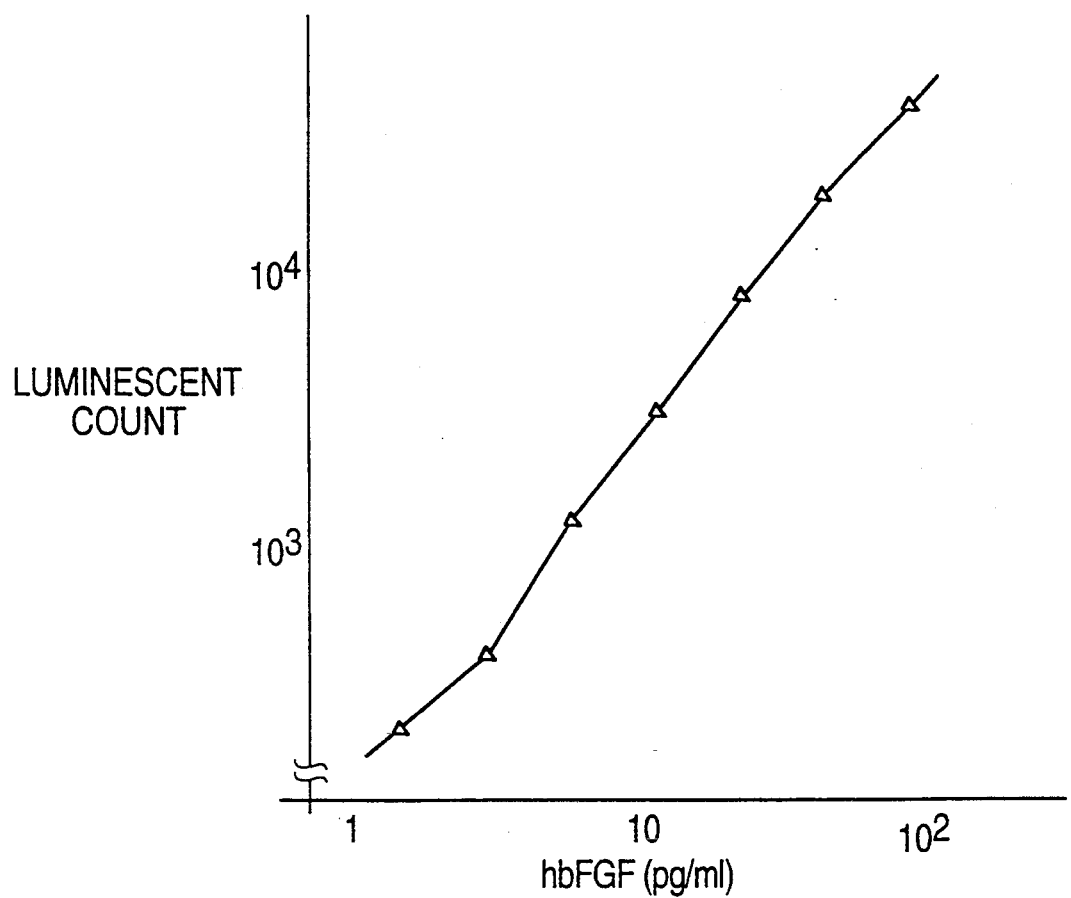
FIG. 3 shows the Calibration Curve prepared using the standard recombinant human bFGF (rhbFGF).

Into each well of the antibody-sensitized plate obtained in [1], 100 μl of sample prepared by mixing 80 μl of bFGF-Zero serum or test sample serum to be analized, 80 μl of a standard solution of the rhbFGF in buffer B or buffer B alone, and 80 μl of buffer B containing 3 mg/ml mouse IgG, 1.5 M NaCl and 60 μg/ml inactivated HRP was poured, followed by reaction at 4° C. for 24 hours. After washing each well with buffer A, 100 μl of the enzyme-labelled antibody solution diluted 300 times with buffer C was added to each well, followed by further reaction at 4° C. for 4 hours. After washing each well with buffer A, 50 μl of a solution of L-012 for luminescence and 50 μl of a 600 μM solution of hydroperoxide were added consecutively thereto, thereby to evoke chemiluminescent reaction. Measurement was conducted by measuring the chemiluminescent amounts in the respective wells. The obtained Calibration Curve of hbFGF is shown in FIG. 3. From the result, it was revealed that about 2 pg/ml of hbFGF in serum could be detected by the method. When the sodium salt of L-012 was used as a substrate instead of L-012, the same sensitivity was obtained.

(c) Amounts of hbFGF in sera of normal humans

Figure 4:
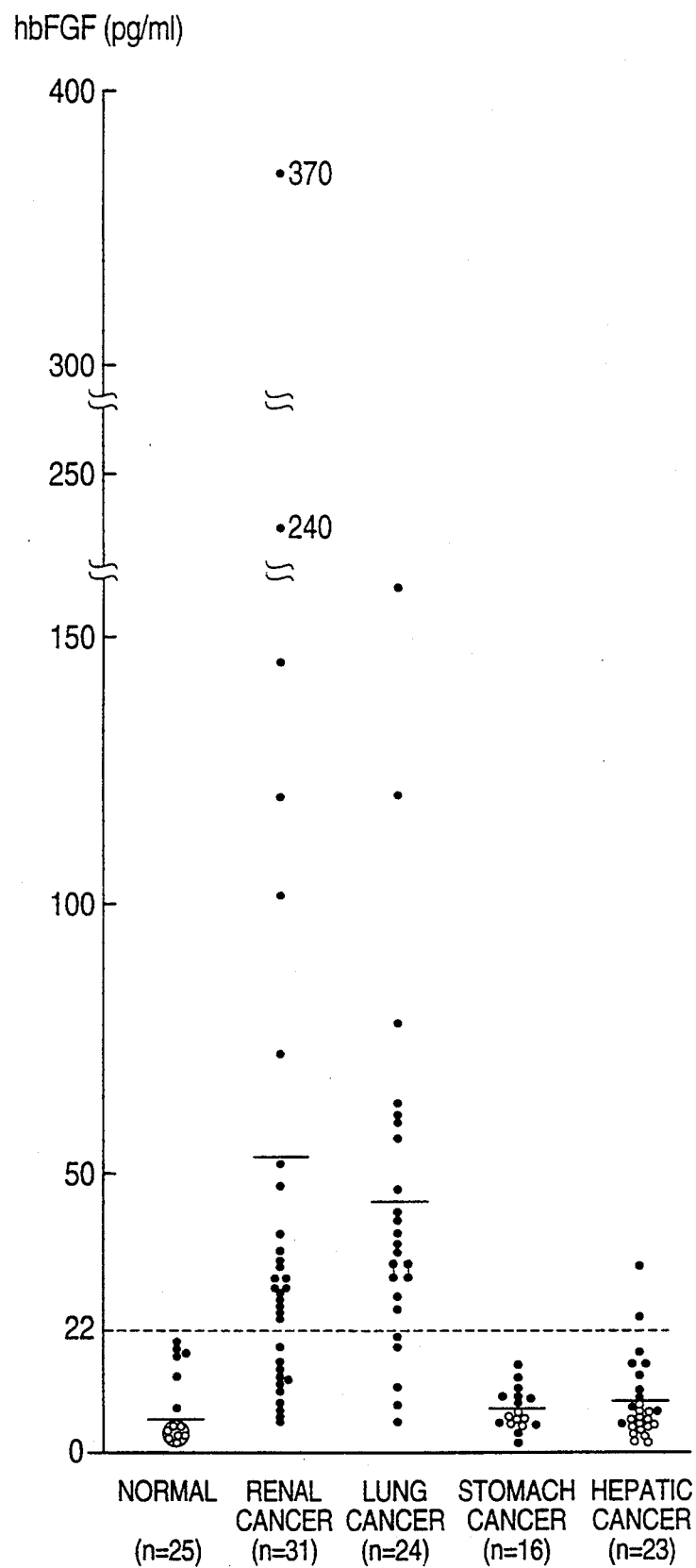
FIG. 4 shows the amounts of the hbFGF in the sera of normal healthy humans and patients bearing various cancers measured in accordance with the assay method of the present invention. The horizontal lines in the lanes are the respective mean values.

The amounts of the hbFGF in the sera of normal healthy humans (n=25) were measured in accordance with the assay method of the present invention. The results are shown in FIG. 4. From the results, it was found that the mean amount of hbFGF in normal humans was 5.9 pg/ml.

(d) Amounts of hbFGF in sera of cancer-bearing patients

The amounts of the hbFGF in the sera of patients bearing various cancers (n=16–31) were measured in accordance with the assay method of the present invention. The results are shown in FIG. 4. The results were further analysed by taking the mean value of the normal healthy human sera +3 standard deviations (22 pg/ml)

as a normal concentration upper limit. Using this cut-off value, 79.2% (21/31) of the lung cancer sera, 67.7% (21/31) of the renal cancer sera, 8.7% (2/23) of the hepatic cancer sera and 0% (0/16) of the stomach cancer sera were positive. That is, it was revealed that in the case of lung cancer and renal cancer, extremely high positive ratios were shown.

We claim:

1. A pyridopyridazine compound of the formula

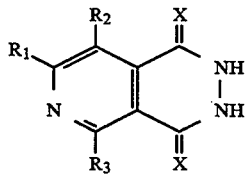

wherein $R_1$ is a hydrocarbon selected from the group consisting of straight chain or branched chain lower alkyl groups having 1 to 6 carbon atoms, alkenyl groups having 2 or 3 carbon atoms, alkynyl groups having 2 or 3 carbon atoms, aralkyl groups having 7 to 12 carbon atoms and aryl groups having 6 to 10 carbon atoms, or a heterocyclic group selected from the group consisting of 2-pyridyl, 4-pyridyl, 2-thienyl, 2-furyl, imidazolyl, triazolyl, tetrazolyl, morpholino, piperazinyl, 4-thiazolyl and 2-amino-4-thiazolyl, wherein $R_1$ can have substituents selected from the group consisting of $R_4$ and $R_4-(CH_2)_n-A-$, wherein $R_4$ is $-CN$, halogen, $-OPO_3M_2$, $-OSO_3M$, $-CO_2R_5$, $-SR_6$, $-OR_6$ or $-NHR_6$ wherein A is a sulfur or oxygen atom, n is an integer of 1 to 4, M is an alkali metal or hydrogen atom, $R_5$ is a hydrogen atom, a lower alkyl group or a group forming an active imido ester capable of forming a conjugate of the formula $-COCH_2CH_2COOR_7$ wherein $R_7$ is selected from the group consisting of maleimido, succinimido and 5-norboren-2,3-carboximido, $R_6$ is a hydrogen atom or succinic acid half ester capable of forming a conjugate of the formula $-COCH_2CH_2COOR_7$ wherein $R_7$ is selected from the group consisting of maleimido, succinimido and 5-norboren-2,3-carboximido;

$R_2$ is hydroxy, thiol, amino, or mono-substituted amino wherein the substituent is selected from the group consisting of straight chain or branched chain lower alkyl having 1 to 6 carbon atoms, alkenyl having 2 or 3 carbon atoms, alkynyl having 2 or 3 carbon atoms, aralkyl having 7 to 12 carbon atoms and aryl having 6 to 10 carbon atoms, and $R_2$ may be taken together with $R_1$ to form a ring selected such that the pyridopyridazine compound has the formula

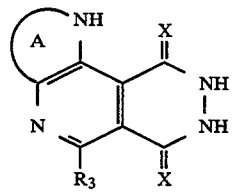

wherein $R_3$ and X are as defined below and ring A is imidazole, or pyrrole;

$R_3$ is hydrogen, hydroxy, alkoxy, aryloxy, aralkyloxy, amino, a mono- or di- substituted amino which has respectively one or two substituents selected from the group consisting of straight chain or branched chain lower alkyl having 1 to 6 carbon atoms, cycloalkyl having 3 to 6 carbon atoms, alkenyl having 2 or 3 carbon atoms, alkynyl having 2 or 3 carbon atoms, aralkyl having 7 to 12 carbon atoms and aryl having 6 to 10 carbon atoms, thiol, alkylthio, arylthio, aralkylthio, halogen, a heterocyclic group selected from the group consisting of 2-pyridyl, 4-pyridyl, 2-thienyl, 2-furyl, imidazolyl, triazolyl, tetrazolyl, morpholino, piperazyl, 4-thiazolyl and 2-amino-4-thiazolyl, nitro, cyano, carboxyl, carbamoyl, alkoxycarbonyl, azido, sulfo, alkylsulfonyl or arylsulfonyl; provided that when $R_3$ is hydrogen, $R_1$ is an aryl group having 6 to 10 carbon atoms which is substituted with $R_4$ or $R_4-(CH_2)-A-$ wherein $R_4$ and A and n are as defined above or a heterocyclic group which may be substituted;

and X is oxygen or sulfur or a salt thereof.

2. The compound according to claim 1, wherein $R_1$ is an aryl group having 6 to 10 carbon atoms or a straight chain or branched chain lower alkyl group having 1 to 6 carbon atoms.

3. The compound according to claim 2, wherein $R_1$ is phenyl or methyl.

4. The compound according to claim 1, wherein $R_2$ is amino or hydroxy.

5. The compound as claimed in claim 1, which is the sodium salt of the compound wherein $R_1$ is phenyl, $R_2$ is amino, $R_3$ is chloro and X is oxygen.

* * * * *

UNITED STATES PATENT AND TRADEMARK OFFICE
CERTIFICATE OF CORRECTION

PATENT NO. : 5,420,275
DATED : May 30, 1995
INVENTOR(S) : Hirotomo MASUYA et al.

It is certified that error appears in the above-indentified patent and that said Letters Patent is hereby corrected as shown below:

In Column 52, line 36, contains a typographical error wherein "$R_4-(CH_2)-A-$" should read --$R_4-(CH_2)n-A$---.

Signed and Sealed this

Nineteenth Day of December, 1995

Attest:

BRUCE LEHMAN

Attesting Officer    Commissioner of Patents and Trademarks